United States Patent [19]

Lee et al.

[11] Patent Number: 5,593,984
[45] Date of Patent: Jan. 14, 1997

[54] CEPHALOSPORIN DERIVATIVES

[75] Inventors: Jong W. Lee, Kwacheon; Jeong S. Chae, Seoul; Young R. Choi, Euiwang; Yeong N. Lee, Suwon; Eun R. Rho, Anyang; Heui I. Kang, Kunpo; Jae W. Hyun, Seoul, all of Rep. of Korea

[73] Assignee: Yuhan Corporation, Seoul, Rep. of Korea

[21] Appl. No.: 411,767

[22] PCT Filed: Sep. 28, 1993

[86] PCT No.: PCT/KR93/00087

§ 371 Date: Mar. 31, 1995

§ 102(e) Date: Mar. 31, 1995

[87] PCT Pub. No.: WO94/07898

PCT Pub. Date: Apr. 14, 1994

[30] Foreign Application Priority Data

Oct. 1, 1992 [KR] Rep. of Korea ............. 92-17969

[51] Int. Cl.⁶ .................... C07D 501/46; A61K 31/545
[52] U.S. Cl. .................... 514/202; 514/205; 540/222; 540/227
[58] Field of Search .................... 540/222, 227; 514/202, 205

[56] References Cited

U.S. PATENT DOCUMENTS 4,788,185  11/1988  Miyake et al. .................... 540/222

Primary Examiner—John M. Ford
Attorney, Agent, or Firm—Anderson Kill & Olick PC

[57] ABSTRACT

The present invention relates to novel cephalosporin derivatives or pharmaceutically acceptable non-toxic salts thereof useful as antibiotics and to processes for the preparation thereof.

wherein:

$R^1$ is a hydrogen or an optionally halogen-substituted $C_{1-3}$ alkyl group, a propargyl group or —$C(R^a)(R^b)COOH$, wherein $R^1$ and $R^b$ are independently a hydrogen or a $C_{1-3}$ alkyl group;

$R^2$, $R^3$, $R^4$, $R^5$, $R^6$ and $R^7$ are independently a hydrogen or halogen or a $C_{1-3}$ alkyl, amino or hydroxy $C_{1-3}$ alkylthio, cyano, carbamoyl, carboxyl, hydroxy $C_{1-3}$ alkyl, nitro, acetyl or formyl group; and Q is CH, N or CCl.

4 Claims, No Drawings

CEPHALOSPORIN DERIVATIVES

This application is a 371 of PCT/KR93/00087, filed Sep. 28, 1993.

TECHNICAL FIELD

The present invention relates to novel cephalosporin derivatives and processes for the preparation thereof; and more particularly, to novel cephalosporin derivatives and pharmaceutically acceptable non-toxic salts thereof, processes for preparing these compounds and to pharmaceutical compositions containing same as active ingredients.

BACKGROUND ART

Antibiotics of cephalosporin series are widely used in therapy for treatment of diseases which are caused by general pathogenic bacteria in mammals including human beings. There have been numerous studies aimed at increasing the efficacy and stability of the antibiotics of cephalosporin series, resulting in the development of various cephalosporin compounds.

For example, U.S. Pat. No. DES. 2,702,501 discloses various cephalosporin derivatives, including autibiotic known as cefotaxime, having a quaternary ammoniomethyl group in 3-position and/or 2-(2-aminothiazol-4-yl)-2-hydroxy (or substituted hydroxy) iminoacetamido group in the 7-position of cephem nucleus.

Among these known cephalosporin antibiotics, a compound known as ceftazidime, which is disclosed in DE U.S. Pat. No. 2,921,316 displays superior antibacterial activities against Gram-negative bacteria such as *Pseudomonas aeruginosa*, while it exhibits relatively inferior antibacterial activities against Gram-positive bacteria, in particular, Staphylococcus species. On the contrary, cefotaxime has been reported to have antibacterial activities against Staphylococcus species, while it possesses less effective antibacterial activities against *Pseudomonas aeruginosa*.

Accordingly, there have ensued further efforts to develop cephalosporin compounds having an excellent activity of broad spectrum, e.g., against both Gram-positive and Gram-negative bacteria including *Pseudomonas aeruginosa*.

For example, European Patent Application No. 47,977 discloses cephalosporin compounds having the following formula(A):

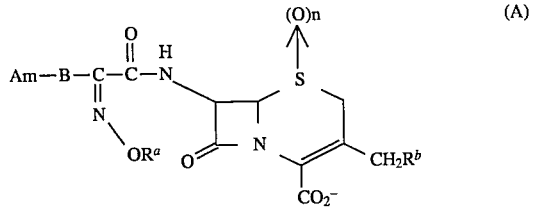

wherein:

n is 0 or 1;

Am is an optionally substituted amino group;

B is a thiadiazolyl group (which is attached to its neighbor group via its two carbon atoms);

$R^a$ is a hydrogen or a cycloalkyl, optionally substituted alkyl or carbamoyl group; and $R^b$ is an optionally substituted thiazolium or pyrazolium, tri(lower)alkyl ammonium, or pyridinium group having the formula of

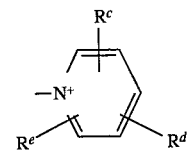

wherein:

$R^c$ is an (lower)alkyl substituted with cycloalkyl, methyl, hydroxy, alkoxy, halogen, cyano, carbamoyl, carboxy or sulfonyl, (lower)alkenyl or (lower)alkylthio optionally substituted with carboxy, amino optionally monosubstituted by (lower)alkyl, (lower)alkanoyl or aminobenzenesulfonyl, di(lower)alkylamino, carbamoyl substituted with (lower)alkyl, hydroxy(lower)alkyl, (lower)alkoxy, hydroxy or cyano, di(lower)alkylcarbamoyl, thiocarbamoyl, cycloalkyl, phenyl, hydroxy, (lower)alkoxy, halogen, (lower)alkoxycarbonyl, (lower)alkanoyloxy, (lower)alkanoyl, carboxy, sulfocyano, nitro or hydroxysulfo(lower)alkyl group;

$R^d$ is a hydrogen or a carbamoyl or the same as $R^c$; and $R^e$ is a hydrogen or the same as $R^c$.

However, search for the desirable antibiotics with The broad spectrum is far from complete.

DISCLOSURE OF INVENTION

Accordingly, a primary object of the present invention is to provide novel cephalosporin derivatives and pharmaceutically acceptable non-toxic salts thereof which have strong antibacterial activities against a broad spectrum of pathogenic bacteria.

It is another object of the present invention to provide processes for preparing the cephalosporin derivatives and pharmaceutically acceptable non-toxic salts thereof.

It is still another object of the present invention to provide pharmaceutical compositions containing the above novel compounds as active ingredients.

In accordance with one aspect of the present invention, there are provided novel cephalosporin derivatives of formula(I) and pharmaceutically acceptable non-toxic salts thereof:

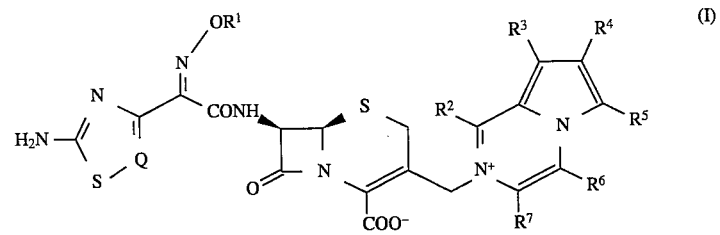

wherein:

$R^1$ is a hydrogen or an optionally halogen-substituted $C_{1-3}$ alkyl group, a propargyl group or —$C(R^a)(R^b)COOH$, wherein $R^a$ and $R^b$ are independently a hydrogen or a $C_{1-3}$ alkyl group;

$R^2$, $R^3$, $R^4$, $R^5$, $R^6$ and $R^7$ are independently a hydrogen or halogen or a $C_{1-3}$ alkyl, amino or hydroxy $C_{1-3}$ alkylthio, cyano, carbamoyl, carboxyl, hydroxy $C_{1-3}$ alkyl, nitro, acetyl or formyl group; and Q is CH, N or CCl.

In accordance with another aspect of the present invention, there are provided processes for preparing the cephalosporin derivatives of formula(I) and pharmaceutically acceptable non-toxic salts thereof.

In accordance with a further aspect of the present invention, there are provided pharmaceutical compositions comprising the cephalosporin derivatives of formula(I) and pharmaceutically acceptable non-toxic salts thereof as active ingredients.

Among the cephalosporin derivatives of the present invention, preferred are those wherein: $R^1$ is a hydrogen or a methyl, ethyl, carboxymethyl, carboxypropyl, fluoromethyl, 2-fluoroethyl or propargyl group; $R^2$ is a hydrogen or a methyl group; $R^3$ is a hydrogen or chlorine or an isopropyl or hydroxymethyl group; $R^4$ and $R^7$ are respectively a hydrogen; $R^5$ is a hydrogen, chlorine or bromine or an isopropyl, hydroxymethyl, hydroxyethyl, hydroxyethylthio, aminoethylthio, cyano, nitro, carbamoyl, carboxyl, acetyl or formyl group; $R^6$ is a hydrogen, or an ethyl or carboxyl group; and Q is CH, N or CCl.

More preferred compounds of formula(I), which have especially high antibacterial activities, are those listed in Table 1 and non-toxic salts thereof.

TABLE 1

Preferred Species of Formula (I) Compounds

| $R^1$ | $R^2$ | $R^3$ | $R^4$ | $R^5$ | $R^6$ | $R^7$ | Q |
|---|---|---|---|---|---|---|---|
| *Me | H | H | H | H | H | H | CH |
| C(Me)$_2$COOH | H | H | H | H | H | H | CH |
| **Et | H | H | H | H | H | H | CH |
| Propargyl | H | H | H | H | H | H | CH |
| CH$_2$CH$_2$F | H | H | H | H | H | H | CH |
| CH$_2$F | H | H | H | H | H | H | CH |
| H | H | H | H | H | H | H | CH |
| Me | H | H | H | S(CH$_2$)$_2$OH | H | H | CH |
| Et | H | H | H | S(CH$_2$)$_2$OH | H | H | CH |
| CH$_2$F | H | H | H | S(CH$_2$)$_2$OH | H | H | CH |
| Me | H | H | H | Cl | H | H | CH |
| Et | H | H | H | Cl | H | H | CH |
| Me | H | H | H | CN | H | H | CH |
| Me | H | H | H | NO$_2$ | H | H | CH |
| Me | H | H | H | CONH$_2$ | H | H | CH |
| Et | H | H | H | CONH$_2$ | H | H | CH |
| Me | H | H | H | COOH | H | H | CH |
| Me | H | H | H | COMe | H | H | CH |
| Et | H | H | H | COMe | H | H | CH |
| Me | H | H | H | CH(Me)OH | H | H | CH |
| Me | H | H | H | CH$_2$OH | H | H | CH |
| CH$_2$F | H | H | H | CH$_2$OH | H | H | CH |
| CH$_2$COOH | H | H | H | CH$_2$OH | H | H | CH |
| C(Me)$_2$COOH | H | H | H | CH$_2$OH | H | H | CH |
| Me | H | H | H | CHO | H | H | CH |
| Et | H | H | H | CHO | H | H | CH |
| Me | H | H | H | S(CH$_2$)$_2$NH$_2$ | H | H | CH |
| Et | H | H | H | S(CH$_2$)$_2$NH$_2$ | H | H | CH |
| CH$_2$F | H | H | H | S(CH$_2$)$_2$NH$_2$ | H | H | CH |
| Me | H | CH$_2$OH | H | H | H | H | CH |
| Et | H | CH$_2$OH | H | H | H | H | CH |
| CH$_2$F | H | CH$_2$OH | H | H | H | H | CH |
| Me | H | Cl | H | H | H | H | CH |
| Me | H | Cl | H | COMe | H | H | CH |
| Et | H | Cl | H | COMe | H | H | CH |
| Me | H | isopropyl | H | isopropyl | H | H | CH |
| Me | H | H | H | H | Et | H | CH |
| Et | H | H | H | H | Et | H | CH |
| Me | H | H | H | H | COOH | H | CH |
| Me | Me | H | H | H | H | H | CH |
| Et | Me | H | H | H | H | H | CH |
| Et | Me | H | H | Br | H | H | CH |
| Me | Me | H | H | CN | H | H | CH |
| Me | Me | H | H | CONH$_2$ | H | H | CH |
| Me | Me | H | H | Cl | H | H | CH |
| Me | Me | H | H | CH$_2$OH | H | H | CH |
| Me | H | H | H | H | H | H | CCl |
| Me | H | H | H | H | H | H | N |
| Me | H | H | H | CH$_2$OH | H | H | CCl |
| Me | H | H | H | CH$_2$OH | H | H | N |
| Me | H | H | H | CH(Me)OH | H | H | N |
| Me | H | H | H | S(CH$_2$)$_2$OH | H | H | CCl |
| Me | H | H | H | S(CH$_2$)$_2$OH | H | H | N |
| Me | H | CH$_2$OH | H | H | H | H | CCl |

TABLE 1-continued

Preferred Species of Formula (I) Compounds

| $R^1$ | $R^2$ | $R^3$ | $R^4$ | $R^5$ | $R^6$ | $R^7$ | Q |
|---|---|---|---|---|---|---|---|
| Me | H | CH$_2$OH | H | H | H | H | N |
| Me | Me | H | H | H | H | H | CCl |
| Me | Me | H | H | H | H | H | N |
| Me | Me | H | H | CH$_2$OH | H | H | CCl |
| Me | Me | H | H | Br | H | H | N |

*Me represents a methyl group.
**Et represents an ethyl group.

The novel cephalosporin compounds of formula(I) include both syn- and anti-isomers and a mixture thereof which contain at least 90% of the syn-isomers when $R^1$ is a $C_{1-3}$ alkyl group.

The compounds of formula(I) also include the diastereomeric isomers and mixtures thereof when $R^1$ is —C($R^a$)($R^b$)COOH, with a further proviso that $R^a$ and $R^b$ are different from each other.

In addition, the compounds of formula(I), and the intermediates useful for their preparation, contain an aminothiazolyl group which may form tautomers with a thiazolinyl group as follows:

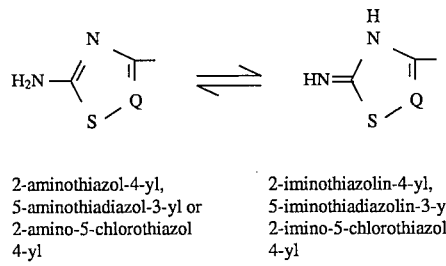

2-aminothiazol-4-yl,
5-aminothiadiazol-3-yl or
2-amino-5-chlorothiazol-4-yl 2-iminothiazolin-4-yl,
5-iminothiadiazolin-3-yl or
2-imino-5-chlorothiazolin-4-yl In the present specification, the partial structures will be summarily represented by the following structure (although the present invention is not limited thereto):

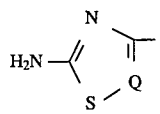

In addition, the compounds of formula(I) contain optionally substituted pyrrolo[1,2-a]pyrazinium-2-yl group at the 3-position of cephem nucleus. For the sake of convenience, positive charge is indicated on the nitrogen atom in the 1-position of pyrazine ring; however, the quaternary nitrogen of the pyrrolo[1,2-a]pyrazinium-2-yl group may be the nitrogen atom at the 4-position of pyrazine ring, or the positive charge may be distributed on a pyrazine ring or even a fused ring. Thus, the pyrrolo [1,2-a]pyrazinium may be represented by the following formula:

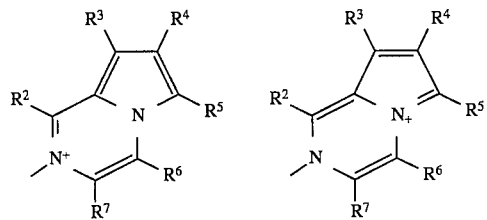

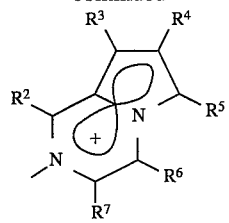

Furthermore, the present invention encompasses within its scope Those pharmaceutically acceptable non-toxic salts of the compounds of formula(I). Suitable pharmaceutically acceptable salts of the cephalosporin compounds(I) are conventional non-toxic salts and may include inorganic acid salts (e.g., hydrochloride, hydrobromide, phosphate, sulfate, etc.); organic carboxylic or sulfonic acid salts (e.g., acetate, trifluoroacetate, citrate, formate, maleate, oxalate, succinate, benzoate, tartarate, fumarate, mandelate, ascotbate, methanesulfonate, benzenesulfonate, p-toluenesulfonate, etc.); and also, depending on $R^1$, inorganic base salts such as alkali metal hydroxides(e.g., sodium hydroxide, potassium hydroxide, etc.), alkaline earth metal hydroxides (e.g., calcium hydroxide, etc.), sodium bicarbonate, potassium bicarbonate, sodium carbonate, potassium carbonate, calcium carbonate, etc. or organic base salts including amino acids.

In addition, conventional acid addition salts used in the field of penicillin or cephalosporin antibiotics may be included. Such acid addition salts may be prepared in accordance with any of the conventional methods.

The present invention also includes within its scope pharmaceutical compositions comprising one or more of the compound(I) and their derivatives as active ingredients, in association with pharmaceutically acceptable carriers, excipients or other additives, if necessary. The compositions may be formulated into various forms such as solution, suspension or emulsion in an oily or aqueous vehicle, which may contain conventional additives such as a dispersant, suspending agent, stabilizer and the like. Alternatively, the active ingredient may be formed into a dried powder that may be dissolved in an aqueous solution of sterile pyrogen-free water before use. The present compounds may be also formulated into suppositories containing conventional suppository bases such as cocoa butter or other glycerides. If desired, the novel compounds can be administered in combination with other antibiotics such as penicillin or other cephalosporins.

The compounds of the present invention may be administered to human beings or animals infected with variety of Gram-positive or Gram-negative bacteria, in an amount ranging from 1 to 50 mg/day, more preferably 1 to 20 mg/day per kg of body weight depending on the age and body weight of the patient, the nature and severity of the illness and so on. The antibiotic compounds of the invention may be formulated for administration in unit dose or multi-dose containers.

The novel compounds(I) of the present invention may be prepared in accordance with process A, B, or C, all of which are described below.

with acetonitrile, acetone, tetrahydrofuran or dioxane, or an inorganic buffer solution such as phosphate buffer solution, which is preferably used in an amount as little as possible.

The reaction may be carried out at a temperature of 40° C. to 100° C., preferably 60° C. to 80° C., for a time period of 30 minutes to 4 hours. If necessary, the pH of the reaction mixture may be adjusted within the range of pH 3 to pH 8 by the addition of inorganic acid such as hydrochloric acid.

The compound of formula(III) may be used in an amount of 1 mole to 10 moles per mole of the compound of formula(II).

Process A

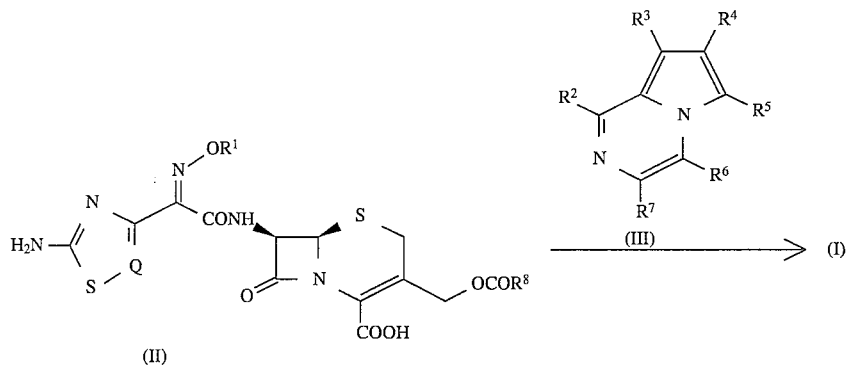

wherein:

$R^1$, $R^2$, $R^3$, $R^4$, $R^5$, $R^6$, $R^7$ and Q have the same meanings as defined above, and $R^8$ is a $C_{1-4}$ alkyl group.

In accordance with process A, the desired compound of formula(I) may be prepared by reacting a compound of formula(II) or its salt with a compound of formula(III). The reaction can be carried out in the presence of an inorganic salt such as sodium iodide, potassium iodide, potassium thiocyanate, etc. or an organic salt such as sodium p-toluene sulfonate in a suitable solvent.

The inorganic salts or organic salts may be used in an amount of about 5 to 30 moles per mole of the compound of formula(II).

Suitable solvents for use in the above reaction may include water, aqueous solvent such as a mixture of water

Process B

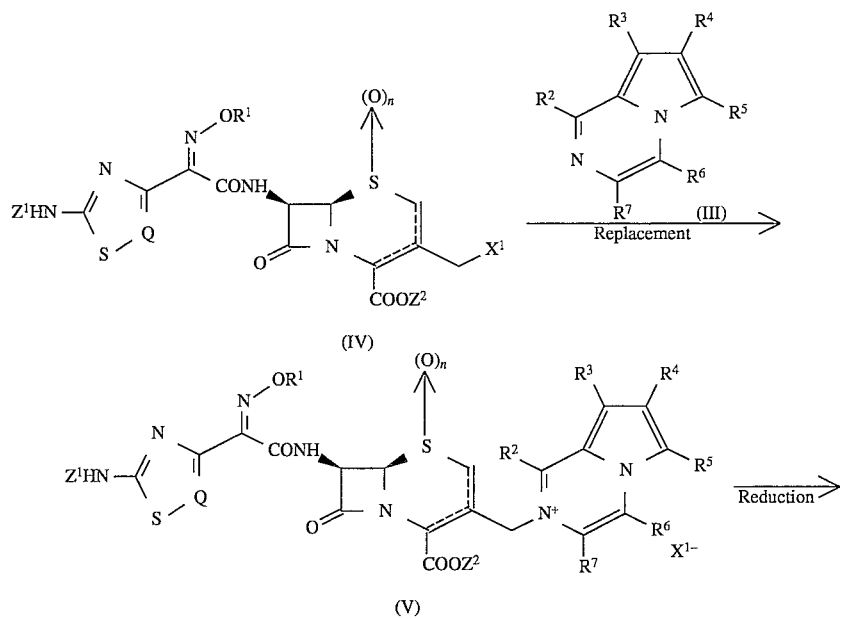

-continued
Process B

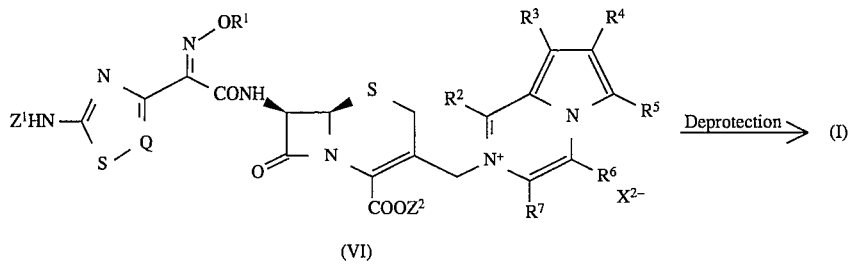

(VI)

wherein:
$R^1, R^2, R^3, R^4, R^5, R^6, R^7$ and Q have the same meanings as defined above, n is 0 or 1, $Z^1$ is a hydrogen or an amino protecting group, $Z^2$ is a carboxy protecting group, and $X^1$ and $X^2$ are independently a leaving group or a halogen atom.

The amino protecting group may include acyl, substituted or unsubstituted aryl(lower)alkyl (e.g., benzyl, diphenylmethyl, triphenylmethyl and 4-methoxybenzyl), halo(lower)alkyl (e.g., trichloromethyl and trichloroethyl), tetrahydropyranyl, substituted phenylthio, substituted alkylidene, substituted aralkylidene or substituted cycloalkylidene and the conventional amino protecting groups.

The acyl group appropriate for an amino protecting group may include, for example, $C_{1-6}$ alkanoyl (e.g., formyl and acetyl), $C_6$ alkoxycarbonyl (e.g., methoxycarbonyl and ethoxycarbonyl), (lower)alkanesulfonyl (e.g., methanesulfonyl and ethanesulfonyl), arenesulfonyl(e.g., benzenesulfonyl, p-toluenesulfonyl), aryl(lower)alkanoyl (e.g., phenylacetyl) or aryl(lower)alkoxycarbonyl (e.g., benzyloxycarbonyl), where the acyl group can be substituted with 1 to 3 substituent(s) such as a halogen or a hydroxy, cyano or nitro group. In addition, the amino protecting group may include reaction products obtained from amino groups and silane, boron or phosphorus compounds.

The carboxy protecting group of $Z^2$ in formula(IV) may include, for example, (lower)alkylesters (e.g., methylester and t-butylester), (lower)alkenylesters(e.g., vinylester and allylester), (lower)alkoxy(lower)alkylesters (e.g., methoxymethylester), (lower)alkylthio(lower)alkylesters (e.g., methylthiomethylester), halo(lower)alkylesters (e.g., 2,2,2-trichloroethylester), substituted or unsubstituted aralkyl-esters (e.g., benzylester and p-nitrobenzylester), and silylesters.

The amino protecting group or the carboxy protecting group may be any group which can be readily removed under the conventional mild conditions such as hydrolysis or reduction to allow the formation of free amino groups or carboxyl groups, and which can be properly selected by considering the chemical properties of the desired compound of formula(I).

The leaving groups of $X^1$ and $X^2$ in formula(IV) may include, for example, a halogen such as chlorine or fluorine, a (lower)alkanoyloxy group such as acetoxy, a (lower)alkanesulfonyloxy group such as methanesulfonyloxy, an arenesulfonyloxy group such as p-toluenesulfonyloxy, an alkoxycarbonyloxy group and the like.

The dotted line in the formula(IV) represents a single or double bond; and therefore, the compounds of formula(IV) may be the compounds of formula(IV-a) or the compounds of formula(IV-b), or mixtures thereof:

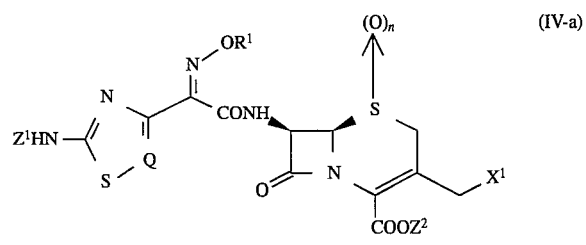

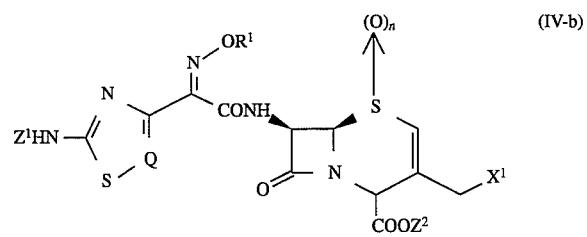

wherein:
$R^1, Q, Z^1, Z^2, X^1$ and n have the same meanings as defined above.

As can be seen from the above reaction scheme, process B comprises a replacement reaction, a reduction reaction and a deprotection reaction.

In the substitution reaction, a compound of formula(IV) is reacted with a compound of formula(III) in an inert solvent such as acetone, methylethylketone, dichloromethane, tetrahydrofuran or acetonitrile, to provide a compound of formula (V). The reaction can be carried out at a temperature of 0° C. to 50° C., preferably to 30° C. for 3 to 24 hours.

In the reduction reaction, the compound of formula(V) obtained in the above reaction is reacted with a deoxygenating agent such as phosphorus trichloride or phosphorus tribromide in an inert solvent such as N,N-dimethylformamide or N,N-dimethylacetamide. The reaction can be carried out at a temperature of –70° C. to 0° C., preferably –50° C. to –20° C. for 30 to 60 minutes.

The deprotection reaction of the compound of formula(VI) obtained in the above reaction is carried out in the presence of an inorganic acid (e.g., hydrochloric acid), an organic acid (e.g., formic acid and trifluoro acetic acid) or a mixture thereof or a scavenger (e.g., anisole or thioanisole) to obtain a desired compound of formula(I). The reaction can be carried out at a temperature of 0° C. to 50° C., preferably 15° C. to 30° C. for 30 minutes to 2 hours.

Process C

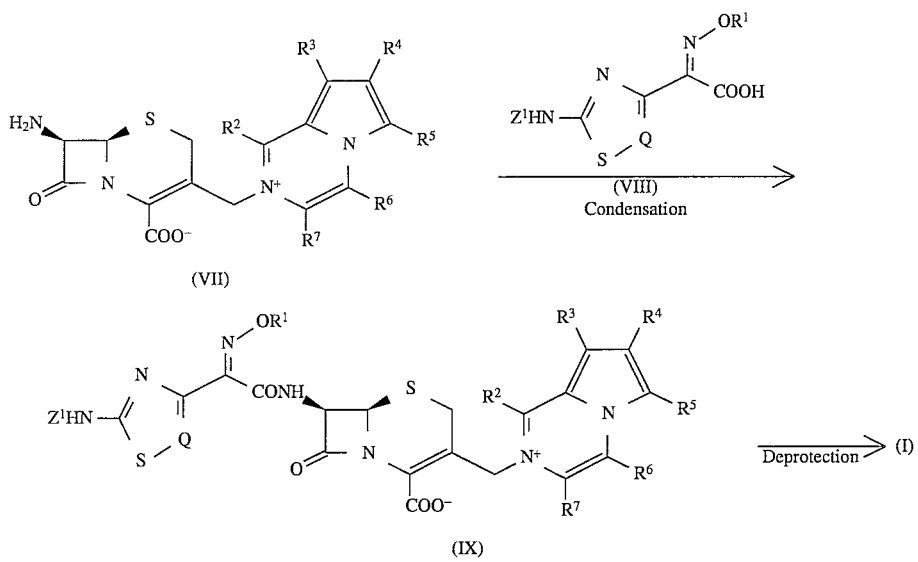

wherein

R$^1$, R$^2$, R$^3$, R$^4$, R$^5$, R$^6$, R$^7$, Q and Z$^1$ have the same meanings as defined above.

As described in the above reaction scheme, process C comprises a condensation reaction and a deprotection reaction.

The condensation reaction of a compound of formula(VII) with a reactive derivative of compound(VIII) may be carried out in the presence of N,O-bis-(trimethylsilyl)acetamide, triethylamine, sodium bicarbonate, sodium carbonate, potassium bicarbonate, potassium carbonate or propylene oxide in an inert solvent such as ethyl acetate, acetonitrile, dichloromethane, etc. to obtain a compound of formula(IX) at a temperature of –50° C. to 50° C.

The reactive derivative of compound(VIII) may be prepared by treating the compound(VIII) with phosphorus pentachloride, thionly chloride, oxalyl chloride, etc. or by treating the compound(VIII) with vilsmeir reagent prepared from N,N-dimethylformamide and phosphorus oxychloride or oxalyl chloride. In addition, one of the reactive derivatives of compound(VIII) may also be prepared by reacting a compound of formula(VIII) with N-hydroxybenzotriazol or benzthiazyl disulfide using a conventional condensation reagent in the presence of an organic solvent such as N,N-dimethylformamide, dichloromethane, tetrahydrofuran, acetonitrile, etc.

The deprotection reaction can be carried out in the same manner as described in process B to obtain a desired compound of formula(I).

The cephalosporin compounds of formula(I) in accordance with the present invention exhibit strong and a broad spectrum of antibacterial activities; and, therefore, can be used for the prevention and treatment of bacterial infections in human beings and animals. Especially, as can be seen from the following Test Example, the cephalosporin compounds of formula(I) exhibit potent antibacterial activities against Gram-positive and Gram-negative bacteria including *Pseudomonas aeruginosa*.

The following Preparation Examples and Examples are provided for purposes of illustrating certain aspects of the present invention only; and are not to be construed as limiting the scope of the present invention in any way.

The terms and abbreviations used in the instant Examples have their normal meaning unless otherwise designated, for example, "°C." refers to degrees celsius; "N" refers to normal or normality; "mmol" refers to millimole; "g" refers to gram; "ml" means milliliter; "M" refers to molar; "NMR" refers to nuclear magnetic resonance; "IR" refers to infrared spectrophotometry; "v/v" means volume per volume; "w/v" refers to weight/volume; and "w/w" means weight per weight.

PREPARATION EXAMPLE 1

Preparation of pyrrolo[1,2-a]pyrazine 1-1) Preparation of 2-pyrrolealdehydeaminoacetal To 24 g of 2-pyrrolecarboxaldehyde was added 100 ml of toluene and then 40.5 ml of aminoacetaldehydedimethylacetal. The reaction mixture was refluxed for 2 hours using Dean-Stark apparatus, concentrated under a reduced pressure and then distilled in vacuo to obtain 45 g of the title compound as a light yellow liquid(yield: 98%)

b.p.: 108°–110° C./1 torr.

NMR(CDCl$_3$, δ) 3.40 (s, 3H), 3.6 (d, 2H), 4.5 (t, 1H), 6.2, 6.45, 6.8 (m, 3H),8.0 (s, 1H)

1-2) Preparation of pyrrolo[1,2-a]pyrazine 20 g of 2-pyrrolealdehydeaminoacetal prepared in step 1-1) was dissolved in 20 ml of cyclohexane, and the resulting solution was added to 150 g of polyphosphoric acid wherein 20 ml of phosphorus oxychloride was dissolved. The reaction mixture was stirred at 120° C. for 20 minutes. and poured into 1.5 L of ice-water; and the resulting solution was washed with benzene. The aqueous layer was adjusted to pH of 7.5 to 8.0 and extracted with benzene(500 ml×3). The organic layer was washed with water and saturated saline solution, and then concentrated under a reduced pressure. The resulting residue was subjected to column chromatography over silica Gel to obtain 5.3 g of title compound as a light yellow liquid (yield: 41%).

NMR(CDCl$_3$, δ) 6.85, 6.97, 7.46, 7.89, 7.58, 8.91

PREPARATION EXAMPLE 2

Preparation of 1-methylpyrrolo[1,2-a]pyrazine

2-1) Preparation of dimethyl-2-acetylpyrroleaminoacetal 25 g of 2-acetylpyrrole was dissolved in 100 ml of toluene, and then 26.9 g of dimethylaminoacetal was added thereto. The resulting solution was heated to reflux for 24 hours using Dean-Stark apparatus. The reaction mixture was concentrated under a reduced pressure and distilled in vacuo(100°–105° C./0.3 torr) to obtain 16.9 g of colorless liquid (yield 36.8%).

NMR(CDCl$_3$, δ) 8.6 (bs, 1H), 6.82 (s, 1H), 6.55 (s, 1H), 6.2 (s, 1H), 4.7 (m,1H), 3.58 (d, 2H), 3.4 (s, 6H),

IR(neat) cm$^{-1}$: 3300, 2925, 1616, 1413, 1123, 1066, 1036

2-2) Preparation of 1-methylpyrrolo[1,2-a]pyrazine 40 ml of glacial acetic acid and 18 ml of concentrated sulfuric acid were mixed, and then heated to 100° C. To the resulting solution was added dropwise dimethyl 2-acetylpyrroleaminoacetal (15.7 g, 80 mmole) dissolved in 20 ml of toluene for 10 minutes. The resulting mixture was stirred at 100° C. for 30 minutes, and then cooled to room temperature. The reaction mixture was diluted with 200 ml of distilled water and adjusted to pH 10 with 10% sodium hydroxide solution with cooling. The solution was extracted three times with 100 ml of ethyl acetate, concentrated under a reduced pressure, and then distilled in vacuo (50°–55° C./0.3 torr) to obtain 7.35 g of light yellow liquid (yield: 69.3%).

NMR(CDCl$_3$, δ) 7.65 (d, 1H), 7.35 (d, 1H), 7.32 (s, 1H), 6.75 (s, 1H), 6.70 (s,1H), 2.62 (s,3H),

IR(neat) cm$^{-1}$: 3113, 1728, 1642, 1610

PREPARATION EXAMPLE 3

Preparation of 6-bromo-1-methyl-pyrrolo[1,2-a]pyrazine 5.0 g of 1-methylpyrrolo[1,2-a]pyrazine prepared in Preparation Example 2 was dissolved in 60 ml of chloroform; and 6.7 g of N-bromosuccinimide was added thereto at 0° C. The reaction mixture was stirred for 30 minutes at the same temperature; and the resulting solution was concentrated. The residue was chromatographed over silica gel to obtain 6.3 g of title compound (yield: 80%).

NMR(CDCl$_3$, δ) 2.95 (s, 3H), 6.88 (s, 1H), 7.25 (s, 1H), 7.52 (d, 1H), 7.77(d,1H)

PREPARATION EXAMPLE 4

Preparation of 6-cyano-1-methylpyrrolo[1,2-a]pyrazine

To a solution of 4.3 g of 6-bromo-1-methylpyrrolo[1,2-a]pyrazine dissolved in 50 ml of N-methylpyrrolidone was added 4.5 g of copper(I) cyanide. The resulting solution was stirred at 150° C. for 5 hours, and then cooled to room temperature. To the reaction mixture was added 100 ml of sodium cyanide solution; and the resulting solution was extracted with ethyl acetate(100 ml×3). The organic layer was concentrated to dryness to obtain 2.5 g of title compound.

NMR(CDCl$_3$, δ) 2.71 (s, 3H), 6.83 (m, 2H), 7.58 (d, 1H), 7.78 (d, 1H)

PREPARATION EXAMPLE 5

Preparation of 6-carbamoyl-1-methylpyrrolo[1,2-a]pyrazine

To 2.0 g of 6-cyano-1-methylpyrrolo[1,2-a]pyrazine prepared in Preparation Example 4 were added 10 ml of water and 5 ml of hydrochloric acid; and the reaction mixture was reacted at 80° C. for 2 hours, cooled to room temperature, extracted with ethyl acetate, and concentrated. The residue was chromatographed over silica gel to obtain 1.0 g of title compound.

NMR(DMSO-d$_6$, δ) 2.57 (s, 3H), 6.93 (q, 2H), 7.48 (d, 1H), 7.85 (d, 1H)

PREPARATION EXAMPLE 6

Preparation of 6- and 8-chloro-1-methylpyrrolo[1,2-a]pyrazine

To a solution of 4.0 g of 1-methylpyrrolo[1,2-a]pyrazine prepared in Preparation Example 2 dissolved in 20 ml of ethyl acetate was added 4.8 g of N-chlorosuccinimide. The reaction mixture was stirred at reflux for 3 hours, and then cooled to room temperature. The reaction mixture was poured into ice-water; and the organic layer was isolated, and then concentrated under a reduced pressure. The residue was chromatographed over silica gel to obtain 0.8 g of 6-chloro compound and 1.2 g of 8-chloro compound.

6-chloro-1-methylpyrrolo[1,2-a]pyrazine

NMR(CDCl$_3$, δ) 2.67 (s, 3H), 6.68 (m, 2H), 7.58 (d, 1H), 7.73 (d, 1H)

8-chloro-1-methylpyrrolo[1,2-a]pyrazine

NMR(CDCl$_3$, δ) 2.93 (s, 3H), 6.88 (s, 1H), 7.26 (s, 1H), 7.52 (d, 1H), 7.78(d,1H)

PREPARATION EXAMPLE 7

Preparation of 6- and 8-bromopyrrolo[1,2-a]pyrazine 2.6 g of pyrrolo[1,2-a]pyrazine prepared in Preparation Example 1 was dissolved in 30 ml of ethyl acetate; and the reaction mixture was cooled to 0° C. To the rection mixture was added 3.9 g of N-bromosuccinimide; and the resulting solution was stirred for 30 minutes. The reaction mixture was poured into water, extracted with ethyl acetate, and then concentrated to dryness to obtain 2.0 g of 6-bromo compound and 2.1 g of 8-bromo comound.

6-bromopyrrolo[1,2-a]pyrazine

NMR(CDCl$_3$, δ) 6.85 (m, 2H), 7.66 (d, 1H), 7.80 (d, 1H), 8.74 (s, 1H)

8-bromopyrrolo[1,2-a]pyrazine

NMR(CDCl$_3$, δ) 6.84 (s, 1H), 7.23 (s, 1H), 7.73 (d, 1H), 7.83 (d, 1H), 8.89(s,1H)

PREPARATION EXAMPLE 8

Preparation of 8-cyanopyrrolo[1,2-a]pyrazine 2 g of 8-bromopyrrolo[1,2-a]pyrazine prepared in Preparation Example 7 was added to a mixture of 2 g of copper(I) cyanide dissolved in 20 ml of N-methylpyrrolidone at 160° C. The reaction mixture was stirred for 10 minutes and cooled to room temperature. The reaction mixture was poured into 100 ml of distilled water, extracted with ethyl acetate (50ml×3), and then concentrated to dryness to obtain 1.2 g of yellowish brown title compound.

NMR(CDCl$_3$, δ) 6.83 (s, 1H), 7.30 (s, 1H), 7.72(d, 1H), 7.83 (d, 1H), 8.90(s,1H)

PREPARATION EXAMPLE 9

Preparation of 8-carbamoylpyrrolo[1,2-a]pyrazine 1 g of 8-cyanopyrrolo[1,2-a]pyrazine prepared in Preparation Example 8 was added To 5 g of polyphosphoric acid. The reaction mixture was stirred at 60° C. for 4 hours, poured into 100 ml of ice-water and extracted with ethyl acetate (50 ml×3). The residue was chromatographed over silica gel to obtain 0.6 g of title compound.

NMR(DMSO-$d_6$, δ) 6.81 (s, 1H), 7.30 (s, 1H), 7.10 (d, 1H), 7.80 (d, 1H), 8.91 (s, 1H)

PREPARATION EXAMPLE 10

Preparation of 8-carboxypyrrolo[1,2-a]pyrazine

To 1 g of 8-cyanopyrrolo[1,2-a]pyrazine prepared in Preparation Example 8 were added 10 ml of concentrated sulfuric acid, 10 ml of acetic acid and 10 ml of distilled water; and the mixture was refluxed for 1 hour. The reaction mixture was cooled and poured into 100 ml of ice-water. The resulting solid was filtered and dried under reduced pressure to obtain 0.5 g of title compound.

NMR(DMSO-$d_6$, δ) 6.80(s, 1H), 7.31 (s, 1H), 7.68 (d, 1H), 7.78 (d, 1H), 8.87 (s, 1H)

PREPARATION EXAMPLE 11

Preparation of 6-(2-amino-ethylthio)-pyrrolo[1,2-a]pyrazine

To the solution of 2.0 g of 6-bromopyrrolo[1,2-a]pyrazine prepared in Preparation Example 7 dissolved in 20 ml of dimethylformamide were added 1.8 g of 2-aminoethanethiol hydrochloride and 1.0 g of potassium carbonate. The reaction mixture was refluxed for 5 hours, poured into 100 ml of ice-water and then extracted with ethyl acetate (50 ml×3). The organic layer was isolated and concentrated to dryness; and the residue was chromatographed over silica gel to obtain 1.5 g of title compound.

NMR(CDCl$_3$, δ) 2.81 (m, 2H), 3.40 (m, 2H), 6.31 (bs, 2H), 6.82 (t, 1H), 7.08 (d, 1H), 7.68 (m, 1H), 8.21 (m, 1H), 8.80(s, 1H)

PREPARATION EXAMPLE 12

Preparation of 6-(2-hydroxyethylthio)pyrrolo[1,2-a]pyrazine 2.5 g of 6-bromopyrrolo[1,2-a]pyrazine prepared in Preparation Example 7 was dissolved in 30 ml of acetonitrile; and 1 ml of 2-thioethanol was added thereto. The reaction mixture was refluxed for 12 hours, cooled to room temperature, poured into ice-water and then extracted with ethyl acetate (50 ml×3). The organic layer was concentrated to dryness under a reduced pressure. The residue was chromatographed over silica gel to obtain 1 g of title compound.

NMR(CDCl$_3$, δ) 2.82 (m, 2H), 3.68 (m, 2H), 4.40(bs, 2H), 6.80 (m, 1H), 7.04(m, 1H), 7.57 (m, 1H), 8.23 (m, 1H), 8.71(s, 1H)

PREPARATION EXAMPLE 13

Preparation of 6-and 8-chloropyrrolo-[1,2-a]pyrazine 3.6 g of pyrrolo[1,2-a]pyrazine prepared in Preparation Example 1 was dissolved in a mixture of 20 ml of dimethyl sulfoxide and 20 ml of ethyl acetate; and 4.8 g of N-chloro succinimide was added thereto. The reaction mixture was stirred at 60° C. for 6 hours, poured into ice-water, extracted with ethyl acetate(100 ml×3), and then concentrated under a reduced pressure. The residue was chromatographed over silica gel to obtain 0.6 g of 6-chloropyrrolo[1,2-a]pyrazine and 0.4 g of 8-chloropyrrolo[1,2-a]pyrazine, respectively.

6-chloropyrrolo[1,2-a]pyrazine

NMR(CDCl$_3$, δ) 6.88 (s, 2H), 7.62 (d, 1H), 7.79(d, 1H), 8.74 (s, 1H)

8-chloropyrrolo[1,2-a]pyrazine

NMR(CDCl$_3$, δ) 6.83 (d, 1H), 6.90 (d, 1H), 7.71(d, 1H), 7.85 (d, 1H), 8.83 (s, 1H)

PREPARATION EXAMPLE 14

Preparation of 8-nitropyrrolo[1,2-a]pyrazine 5.5 g of pyrrolo[1,2-a]pyrazine prepared in Preparation Example 1 was dissolved in 10 ml of glacial acetic acid; and to the resulting mixture was added dropwise a mixture of sulfuric acid/nitric acid (15 ml/15 ml) at 0° C. The reaction mixture was stirred at room temperature for 30 minutes, poured into 200 ml of ice-water, and then adjusted to pH 10 with sodium hydroxide solution. The resulting solution was extracted with ethyl acetate (100 ml×3), and concentrated to dryness to obtain 4.3 g of title compound.

NMR(CDCl$_3$, δ) 7.35 (d, 1H), 7.53 (d, 1H), 7.78(s, 2H), 9.73 (s, 1H)

PREPARATION EXAMPLE 15

Preparation of 8- and 6-acetyl-pyrrolo[1,2-a]pyrazine 20 g of pyrrolo[1,2-a]pyrazine prepared in Preparation Example 1 was dissolved in 100 ml of dichloroethane; and 30 g of aluminium trichloride and 12 g of acetylchloride were added thereto. The mixture was reacted at 60° C. for 4 hours, cooled to room temperature and then poured into 300 ml of ice-water. The mixture was adjusted to pH 10 with sodium hydroxide, extracted with 500 ml of ethyl acetate and concentrated. The residue was chromatographed over silica gel to obtain 4.5 g of 6-acetylpyrrolo[1,2-a]pyrazine and 4.0 g of 8-acetylpyrrolo-[1,2-a]pyrazine.

6-acetylpyrrolo[1,2-a]pyrazine

NMR(CDCl$_3$, δ) 2.57 (s, 3H), 7.20 (d, 1H), 7.34(d, 1H), 7.76 (d, 1H), 7.92(d, 1H), 9.64 (s, 1H)

8-acetylpyrrolo[1,2-a]pyrazine

NMR(CDCl$_3$, δ) 2.60 (s, 3H), 6.85 (d, 1H), 7.54(d, 1H), 7.90 (d, 1H), 9.03 (s, 1H), 9.55 (d, 1H)

PREPARATION EXAMPLE 16

Preparation of 6-acetyl-8-chloropyrrolo[1,2-a]pyrazine 0.5 g of 6-acetylpyrrolo[1,2-a]pyrazine prepared in Preparation Example 15 was dissolved in 5 ml of chloroform; and 0.5 g of N-chlorosuccinimide was added threrto. The reaction mixture was refluxed for 2 hours and then concentrated. The residue was chromatographed over silica gel to yield 0.5 g of title compound.

NMR(CDCl$_3$, δ) 2.60 (s, 3H), 7.22 (s, 1H), 8.01 (s, 1H), 9.72 (s, 1H)

PREPARATION EXAMPLE 17

Preparation of 6-(1-hydroxyethyl)pyrrolo[1,2-a]pyrazine 2.0 g of 6-acetylpyrrolo[1,2-a]pyrazine prepared in Preparation Example 15 was added to 30 ml of water; and 0.5 g of sodium borohydride was added thereto. After reacting at 50° C. for 2 hours, the mixture was extracted with ethyl acetate (50 ml×3). The residue was chromatographed over silica gel to yield 1.4 g of 6-(1-hydroxyethyl)pyrrolo[1,2-a]pyrazine.

NMR(CDCl$_3$, δ) 1.63 (d, 3H), 3.40 (bs, 1H), 5.34 (q, 1H), 6.83 (s, 1H), 7.35 (m, 2H), 7.72 (d, 1H), 8.90 (s, 1H)

PREPARATION EXAMPLE 18

Preparation of 6- and 8-hydroxymethylpyrrolo[1,2-a]pyrazine 2.5 g of pyrrolo[1,2-a]pyrazine prepared in Preparation Example 1 was added to water (20 ml)/hydrochloric acid (5 ml) mixture. To the mixture was added 7 ml of 36% formalin solution; and the reaction mixture was stirred at 60° C. for 4 hours, cooled to room temperature and then neutralized with aqueous NaOH solution. The reaction mixture was extracted with ethyl acetate (50 ml×3) to isolate the organic layer. The organic layer was dried and then concentrated. The residue was chromatographed over silica gel to obtain 0.5 g of 6-hydroxymethyl compound and 1.0 g of 8-hydroxymethyl compound.

6-hydroxymethylpyrrolo[1,2-a]pyrazine

NMR(CDCl$_3$, δ) 4.31 (bs, 1H), 4.91 (s, 2H), 6.70(d, 1H), 6.79(d, 1H), 7.30 (d, 1H), 7.90 (d, 1H), 8.57 (s, 1H)

8-hydroxymethylpyrrolo[1,2-a]pyrazine

NMR(CDCl$_3$, δ) 4.35 (bs, 1H), 4.80 (s, 2H), 6.73(d, 1H), 6.83(d, 1H), 7.40 (d, 1H), 8.01(d, 1H), 8.60 (s, 1H)

PREPARATION EXAMPLE 19

Preparation of 6-formylpyrrolo[1,2-a]pyrazine 7.28 of 6-hydroxymethylpyrrolo[1,2-a]pyrazine prepared in Preparation Example 18 was dissolved in 400 ml of dioxane; and 10 g of manganese(IV) dioxide was added thereto. The reaction mixture was refluxed for 30 minutes and then cooled to room temperature. The resulting solution was filtered; and the filtrate was concentrated under a reduced pressure to yield 5.3 g of title compound.

NMR(CDCl$_3$, δ) 6.85 (d, 1H), 7.52 (d, 1H), 7.95(d, 1H), 9.06(s, 1H), 9.38 (d, 1H), 9.92 (s, 1H)

PREPARATION EXAMPLE 20

Preparation of 4-carboxypyrrolo[1,2-a]pyrazine 1.0 g of pyrrolo[1,2-a]pyrazine prepared in Preparation Example 1 was dissolved in 10 ml of tetrahydrofuran and then cooled to −78° C. under nitrogen atmosphere. To the resulting solution was added 1.2 equivalents of LDA (prepared from n-butyl lithium and diisopropylamine) solution. The reaction mixture was stirred at the same temperature for 30 minutes and then carbon dioxide gas was bubbled into the mixture for 10 minutes. The reaction mixture was warmed to room temperature, poured into water and then extracted with 10% methanol-ethyl acetate. The organic layer was concentrated to dryness to obtain 0.3 g of title compound.

NMR(DMSO-d$_6$, δ) 6.88 (s, 2H), 8.24 (s, 1H), 8.83 (s, 1H), 8.96(s, 1H)

PREPARATION EXAMPLE 21

Preparation of 4-ethylpyrrolo[1,2-a]pyrazine 1.0 g of pyrrolo[1,2-a]pyrazine prepared in Preparation Example 1 was dissolved in 10 ml of tetrahydrofuran and then cooled to −78° C. under nitrogen atmosphere. To this solution was added 1.2 equivalents of LDA solution; the resulting mixture was stirred for 30 minutes; and 1 ml of iodoethane was added to the mixture while maintaining the temperature of −78° C. The reaction mixture was stirred for 30 minutes, warmed to room temperature and then poured into water. The organic layer was isolated and then concentrated to dryness to obtain 0.3 g of title compound.

NMR(CDCl$_3$, δ) 1.4 (t, 3H), 2.78 (q, 2H), 6.76(m, 1H), 6.84(m, 1H), 7.30 (m, 2H), 8.68 (s, 1H)

PREPARATION EXAMPLE 22

Preparation of 6,8-diisopropylpyrrolo[1,2-a]pyrazine

To 5 g of pyrrolo[1,2-a]pyrazine prepared in Preparation Example 1 dissolved in 10 ml of isopropylchloride was added 1.2 g of aluminium trichloride. The resulting mixture was reacted at 60° C. for 4 hours, cooled to room temperature and then poured into ice-water. The reaction mixture was adjusted to pH 10 with aqueous NaOH solution, extracted with ethyl acetate (50 ml×3) and then concentrated. The residue was chromatographed over silica gel to obtain 2.0 g of title compound.

NMR(CDCl$_3$, δ) 2.40 (d, 12H), 3.18 (q, 1H), 3.38(q, 1H), 6.58(s, 1H), 7.40 (d, 1H), 7.54 (d, 1H), 8.78 (s, 1H)

PREPARATION EXAMPLE 23

Preparation of 6-hydroxymethyl-1-methylpyrrolo[1,2-a]pyrazine 3 g (22.7 mmol) of 1-methylpyrrolo[1,2-a]pyrazine prepared in Preparation Example 2 was dissolved in water (15 ml)/concentrated hydrochloric acid (35 ml) mixture while cooling with ice-water. The resulting solution was heated to 70° C.; and 60 ml of formalin was added dropwise thereto over 40 minutes. The resulting solution was stirred at 75° C. for 30 minutes, cooled to 0° C. and then neutralized to pH8.0 with sodium hydroxide and sodium bicarbonate. The reaction mixture was extracted with ethyl acetate (100 ml×3), dried over MgSO$_4$ and then concentrated. The residue was chromatographed over silica gel to obtain 1.8 g of title compound (yield: 48.9%).

NMR(DMSO-d$_6$, δ) 2.58 (s, 3H), 4.82 (bs, 1H), 4.95 (s, 2H), 6.70(d, 2H) 7.37 (d, 1H), 7.79 (d, 1H)

PREPARATION EXAMPLE 24

Preparation of 7-amino-3-(pyrrolo-[1,2-a]pyrazinium-2-yl)methyl-3-cephem-4-carboxylate.HI 2.5 g of 7-amino-3-iodomethyl-3-cephem-4-carboxylate was suspended in 30 ml of acetonitrile; and 2 ml bistrimethyl-silylacetamide was added thereto. To the mixture was added 2 g of pyrrolo[1,2-a]pyrazine prepared in Preparation Example 1. The reaction mixture was reacted at 10° C. for 1 hour and then cooled to 0° C. To this solution was added 0.6 ml of water; and the resulting mixture was filtered and then washed with 30 ml of cold acetonitrile to obtain 2.4 g of light yellow title compound (yield: 93%).

NMR (DMSO-d$_6$+TFA-d, δ) 3.3(q,2H), 5.0(s,2H), 5.5(q, 2H), 7.1, 7.4, 7.9, 8.1, 8.9 (Ar-H,6H)

PREPARATION EXAMPLE 25

Preparation of 7-amino-3-[6-hydroxymethylpyrrolo[1,2-a]pyrazinium-2-yl]methyl-3-cephem-4-carboxylate.HI The same procedures as described in Preparation Example 24 were repeated using 6-(hydroxymethyl)pyrrolo[1,2-a]pyrazine prepared in Preparation Example 18 to obtain title compound (yield: 87%).

NMR (DMSO-d$_6$+TFA-d, δ) 3.57(g, 2H, C$_2$—H), 4.92(s, 2H, CHOH), 5.23 (s, 2H, C$_{6,7}$—H), 5.38(g, 2H,C'$_3$—H), 7.36 (d,1H), 7.66(d, 1H), 7.75(d, 1H), 8.68(d, 1H), 9.51(s, 1H$^-$)

PREPARATION EXAMPLE 26

Preparation of 7-amino-3-[6-(1-hydroxyethyl)pyrrolo[1,2-a]pyrazinium-2-yl]methyl-3-cephem-4-carboxylate.HI The same procedures as described in Preparation Example 24 were repeated using 8-(hydroxyethyl)pyrrolo[1,2-a]pyrazine prepared in Preparation Example 17 to obtain title compound (yield: 89%).

NMR (DMSO-d$_6$+TFA-d, δ) 1.49(d, 3H), 3.58(g, 2H, C$_2$—H), 5.22(s,2H, C$_{6,7}$—H, 5.31(g, 2H, C'$_3$—H), 5.39(g, 1H), 7.36(d, 1H), 7.64(d, 1H), 8.39(s, 1H), 8.71 (d, 1H), 9.64(s, 1H)

PREPARATION EXAMPLE 27

Prepration of 7-amino-3-[6-(2-hydroxyethylthio)pyrrolo[1,2-a]pyrazinium-2-yl]methyl-3-cephem-4-carboxylate.HI The same procedures as described in Preparation Example 24 were repeated using 6-(2-hydroxyethylthio)pyrrolo[1,2-a]pyrazine prepared in Preparation Example 12 to obtain title compound (yield: 90%).

NMR (DMSO-d$_6$, +TFA-d, δ) 2.60 (m, 2H), 3.58 (q, 2H), 3.68 (m, 2H), 4.40 (bs, 2H), 5.22 (s, 2H), 5.31 (q, 2H), 5.39 (q, 1H), 6.80 (m, 1H), 7.04 (m, 1H, 7.57 (m, 1H), 8.23 (m, 1H), 8.71 (s, 1H)

PREPARATION EXAMPLE 28

Preparation of 7-amino-3-(8-hydroxymethylpyrrolo[1,2-a]pyrazinium-2-yl)methyl-3-cephem-4-carboxylate.HI The same procedures as described in Preparation Example 24 were repeated using 8-(hydroxymethyl)pyrrolo[1,2-a]pyrazine prepared in Preparation Example 18 to obtain title compound (yield: 92%).

NMR (DMSO-d$_6$+TFA-d, δ) 3.58(g, 2H, C$_2$—H), 4.97(s, 2H, CH$_2$ OH), 5.31 (s, 2H, C$_{6,7}$—H), 5.41(g,2H, C'$_3$—H), 7.40(m, 1H),7.75(m, 1H), 7.83(m, 1H), 8.70 (m, 1H), 9.54(m, 1H).

PREPARATION EXAMPLE 29

Preparation of 7-amino-3-(1-methylpyrrolo[1,2-a]pyrazinium-2-yl)methyl-3-cephem-4-carboxylate.HI The same procedures as described in Preparation Example 24 were repeated using 1-methylpyrrolo[1,2-a]pyrazine prepared in Preparation Example 2 to obtain title compound (yield: 85%).

NMR (DMSO-d$_6$+TFA-d, δ) 3.05(s, 3H, Me), 3.60(g, 2H, C$_2$—H), 5.27(d, 2H, C$_{6,7}$—H), 5.41(g, 2H, C'$_3$—H), 7.35(m, 1H), 7.71(d, 1H), 7.96(m,1H), 8.39(d,1H), 8.73(m,1H)

PREPARATION EXAMPLE 30

Preparation of 7-amino-3-(6-hydroxymethyl-1-methylpyrrolo[1,2-a]pyrazinium-2-yl)methyl-3-cephem-4-carboxylate.HI 2.0 g (5.89mmol) of 3-iodomethylcephem was suspended in 25 ml of acetonitrile; and 2.2 ml of N,O-bistrimethylsilylacetamide was added thereto. To the reaction mixture cooled to 0° C. was added dropwise tho solution of 6-hydroxymethyl-1-methylpyrrolo[1,2-a]pyrazine(1.0 g, 6.16 mmol) dissolved in 10 ml of acetonitrile over 20 minutes; and the reaction mixture was stirred at the same temperature for 30 minutes. 2 ml of methanol was added thereto and was stirred for additional 20 minutes. The resulting precipitates were filtered and washed with 20 ml of acetone to obtain 2.1 g of title compound (yield: 71%).

NMR (DMSO-d$_6$+TFA-d, δ) 3.05 (s, 3H), 3.56 (q, 2H), 4.92 (s, 2H), 5.21(q, 2H), 7.41 (d, 1H), 7.76 (d, 1H), 7.81 (d, 1H), 8.71 (d, 1H)

PREPARATION EXAMPLE 31

Preparation of 7-amino-3-(6-bromo-1-methylpyrrolo[1,2-a]pyrazinium-2-yl)methyl-3-cephem-4-carboxylate.HI The same procedures as described in Preparation Example 30 were repeated using 6-bromo-1-methylpyrrolo[1,2a]pyrazine prepared in Preparation Example 3 to obtain title compound (yield: 82%).

NMR (DMSO-d$_6$+TFA-d, δ) 3.02(s, 3H, Me), 3.58(g, 2H, C$_2$—H),4.95 (d,1H, C$_6$—H), 5.12(d, 1H, C$_7$—H), 5.42(g, 2H, C'$_3$—H), 7.61 (d, 1H), 7.92(d, 1H), 8.12(d, 1H), 8.61(d, 1H)

EXAMPLE 1-1

Preparation of 7-β-[(Z)-2-(2-aminothiazol-4-yl)2-methoxyiminoacetamido]-3-(pyrrolo[1,2a]pyrazinium-2-yl)methyl-3-cephem-4-carboxylate 500 mg of 7-amino-3-(pyrrolo[1,2-a]pyrazinium-2-yl)methyl-3-cephem-4-carboxylate prepared in Preparation Example 24 and 500 mg of 2-(2-aminothiazol-4-yl)-2-methoxyimino)acetic acid-N-hydroxybenzotriazol active compound were added to water (10 ml)/acetonitrile (10 ml) mixture. The reaction mixture was stirred at 35° C. to 40° C. for 4 hours while maintaining the pH thereof between 7.0 and 7.5 by the addition of saturated sodium bicarbonate solution. The reaction mixture was cooled to a room temperature and filtered to remove insoluble materials. The filtrate was chromatographed over silica gel with acetonitrile: distilled water 4:1 (v/v) as eluent and then lyophilized to obtain 300 mg of title compound as light yellow solid.

m.p.: 206° C.(decomposed)

NMR (DMSO-d$_6$, δ): 3.5 (s, 2H), 3.55 (q, 2H), 3.95 (s, 3H), 5.2 (q, 2H), 5.3 (1H, C$_6$—H), 5.9 (1H, C$_7$—H), 6.95 (1H, CH), 7.4, 7.7, 8.4. 8.8, 9.55(5H, Ar—H)

IR KBr (ν$_{c=o}$): 1747.4cm$^{-1}$

EXAMPLE 1-2

Preparation of 7-β-[(Z)-2-(2-aminothiazol-4-yl)2-methoxyiminoacetamido]-3-(pyrrolo[1,2-a]pyrazinium-2-yl)methyl-3-cephem-4-carboxylate The same procedures as described in Example 1-1 were repeated using 500 mg of benzthiazyl sulfide active compound in place of N-hydroxybenzotriazol active compound to obtain 200 mg of title compound.

m.p.: 206° C.(decomposed)

NMR (DMSO-d$_6$, δ): 3.5 (s, 2H), 3.55(q,2H), 3.95(s, 3H), 5.2(q, 2H), 5.3(1H, C$_6$—H), 5.9(1H, C$_7$—H), 6.95(1H, CH), 7.4, 7.7, 8.4. 8.8, 9.55 (5H,Ar—H)

IR KBr (ν$_{c=o}$): 1747.4cm$^{-1}$

EXAMPLE 1-3

Preparation of 7-β-[(Z)-2-(2-aminothiazol-4-yl)2-methoxyiminoacetamido]-3-(pyrrolo[1,2-a]pyrazinium-2-yl)methyl-3-cephem-4-carboxylate Cefotaxime (35.3 g, 77.79 mmol) and N,O-bis(trimethylsilyl)trifluoroacetamide (BSTFA)(64 g, 248.6 mmol) were suspended in 180 ml of dichloromethane; and the resulting mixture was refluxed for 10 minutes. The reaction mixture was cooled room temperature; iodotrimethylsilane (50 g, 249.8 mmol) was added thereto; and then the mixture was stirred at room temperature for 1 hour and concentrated under a reduced pressure. The residue was diluted with acetonitrile (75 ml) and bistrimethylsilylacetamide (30 ml); and the resulting solution was added dropwise 9.2 g of pyrrolo[1,2-a]pyrazine for 30 minutes. The resulting solution was stirred for 30 minutes; acetonitrile (150 ml) and distilled water (20 ml) were added thereto; and the solution was stirred for additional 30 minutes in ice-water and filtered. The combined solid (HI salt) was washed with 200 ml of acetone and then dried in vacuo. The resulting HI salt was dissolved with aqueous $NaHC_3$ solution and chromatographed over silica gel with acetonitrile:distilled water 4:1 (v/v) as eluent, concentrated under a reduced pressure and then lyophilized to obtain 13 g of title compound.

m.p.: 206° C.(decomposed)

NMR (DMSO-$d_6$, δ): 3.5 (s, 2H), 3.55(q,2H), 3.95(s, 3H), 5.2(q, 2H), 5.3(1H, $C_6$—H), 5.9(1H, $C_7$—H), 6.95(1H, CH), 7.4, 7.7, 8.4. 8.8, 9.55(5H, Ar—H)

IR KBr ($v_{c=0}$): 1747.4cm$^{-1}$

EXAMPLE 1-4

Preparation of 7-β-[(Z)-2-(2-aminothiazol-4-yl)2-methoxyiminoacetamido]-3-(pyrrolo[1,2-a]pyrazinium-2-yl)methyl-3-cephem-4-carboxylate 7-Amino-3-(pyrrolo[1,2-a]pyrazinium-2-yl)methyl-3-cephem-4-carboxylate (2.0 g, 6.06 mmol) prepared in Preparation Example 24 was suspended in a mixture of water (5 ml) and distilled water (20 ml); and triethylamine (1 ml, 7.17 mmol) was added thereto. To the reaction mixture cooled to −5° C. to 0° C. was added (Z)-2-(2-aminothiazol-4-yl)-2-methoxyiminoacethyl-chloride hydrochloride (2.3 g, 6.98 mmol) over 15 minutes; and the resulting mixture was stirred for 30 minutes. The reaction mixture was washed with ethylacetate (20 ml×2); and the isolated aqueous layer was chromatographed over silica gel. The aliquots were concentrated under a reduced pressure and lyophilized to yield 2.6 g of title compound.

m.p.: 206° C.(decomposed)

NMR (DMSO-$d_6$, δ): 3.5 (s, 2H), 3.55(q,2H), 3.95(s, 3H), 5.2(q, 2H), 5.3(1H, $C_6$—H), 5.9(1H, $C_7$—H), 6.95(1H, CH), 7.4, 7.7, 8.4. 8.8, 9.55 (5H, Ar–H)

IR KBr ($v_{c=0}$): 1747.4cm$^{-1}$

EXAMPLE 1-5

Preparation of 7-β-[(Z)-2-(2-aminothiazol-4-yl)2-methoxyiminoacetamido]-3-(pyrrolo[1,2-a]pyrazinium-2-yl)methyl-3-cephem-4-carboxylate hydrosulfate 150 g of HI salt prepared in Example 1-3 was suspended in a mixture of water (300 ml), Amberlite LA-2 ion exchange resin (Rohm & Hags Co., U.S.A) (100 ml) and toluene (230 ml) for 1 hour. The aqueous layer was isolated, concentrated under a reduced pressure, passed through IRA-904 exchange resin (Sigma, U.S.A.) (100 ml) and then cooled to 0° C. The aqueous layer was adjusted to pH 2.2 with 6N sulfuric acid and; 600 ml of isopropylalcohol was added thereto. The reaction mixture was stirred at 0° C. for 2 hours and filtered. The filtered solid was washed with 500 ml of acetone and 500 ml of diethylether and then dried in vacuo (yield: 40 g of $H_2SO_4$ salt).

m.p.: 206° C.(decomposed)

NMR (DMSO-$d_6$, δ): 3.5 (s, 2H), 3.55(q,2H), 3.95(s, 3H), 5.2(q, 2H), 5.3(1H, $C_6$—H), 5.9(1H, $C_7$—H), 6.95(1H, CH), 7.4, 7.7, 8.4. 8.8, 9.55 (5H, Ar—H)

IR KBr ($v_{c=0}$): 1747.4cm$^{-1}$

EXAMPLE 2

Preparation of 7-β-[(Z)-2-(2-aminothiazol-4-yl)-2-(2-carboxyprop-2-oxyimino)acetamido]-3-(pyrrolo[1,2-a]pyrazinium-2-yl)methyl-3-cephem-4-carboxylate The same procedures as described in Example 1-1 were repeated using 1 g of 2-benzthiazol 2-(2-aminothiazol-4-yl)-2-(t-butoxycarbonyl-2-prop-2-oxyimino)thioacetate in place of 2-(2-aminothiazol-4-yl)-2-(methoxyimino)aceticacid-N-hydroxy benzotriazol active compound to obtain light yellow solid. The resulting solid was treated with 1 ml of trifluoroacetic acid and 1 ml of anisole to remove t-butoxy group and then chromatographed over silica gel to obtain 200 mg of title compound as pale yellow solid.

m.p.: 228° C.(decomposed)

NMR(DMSO-$d_6$, δ) 1.6 (ss, 6H), 3.6 (q, 2H), 5.4(q, 2H), 5.3 (1H, $C_6$—H), 6.0 (1H, $C_7$—H), 7.05 (1H, CH), 7.4, 7.7, 7.8, 8.4 .8.8, 9.55 (6H, Ar—H)

IR KBr ($v_{c=0}$) 1747.4cm$^{-1}$ 7-8-[(Z)-2-(2-aminothiazol-4-yl)-2-(substituted oxyimino)acetamido]-3-(substituted pyrrolo[1,2-a]pyrazinium-2-yl)methyl-3-cephem-4-carboxylates obtained in the following Examples 3 to 59 were prepared by reacting the corresponding intermediates of substituted pyrrolo[1,2-a]pyrazine with the corresponding (2-aminothiazol-4-yl)-2-substituted oxyimino acetic acid active compound in accordance with the same procedures as described in Example 1-1. Physical properties (m.p., NMR and IR data) of each compound obtained in Example 3 to 59 are given below.

EXAMPLE 3

Preparation of 7-β-[(Z)-2-(2-aminothiazol-4-yl)-2-ethoxyiminoacetamido]-3-(pyrrolo[1,2-a]pyrazinium-2-yl)methyl-3-cephem-4-carboxylate m.p.: 189° C.(decomposed)

NMR (DMSO-$d_6$, δ) 1.2 (t, 3H), 3.55 (q, 2H), 4.2 (m, 2H), 5.3 (q, 2H), 5.2$C_6$—H), 5.9 (1H, $C_7$—H), 6.95 (1H, CH),7.4, 7.7, 8.4, 8.8, 9.55 (6H, Ar—H)

IR KBr ($v_{c=0}$) 1747.4cm$^{-1}$

EXAMPLE 4

Preparation of 7-β-[(Z)-2-(2-aminothiazol-4-yl)-2-(propyn-1-oxyimino)acetamido]-3-(pyrrolo[1,2-a]pyrazinium-2-yl) methyl-3-cephem-4-carboxylate m.p.: 200° C.(decomposed)

NMR (DMSO-$d_6$, δ) 3.2 (m, 3H), 4.5 (s,2H), 4.9 (br, 3H), 5.2 (1H, $C_6$—H), 5.6 (1H, $C_7$—H), 6.75 (1H, CH), 7.1, 7.4, 8.1, 8.5, 9.2 (6H, Ar—H

IR KBr ($v_{c=0}$) 1750.1cm$^{-1}$

EXAMPLE 5

Preparation of 7-β-[(Z)-2-(2-aminothiazol-4-yl)-2-(2-fluoroethoxyimino)acetamido]-3-(pyrrolo[1,2-a]pyrazinium-2-yl)methyl-3-cephem-4-carboxylate m.p.: 216° C.(decomposed)

NMR (DMSO-$d_6$, δ) 3.6 (q, 2H), 4.5 (d,2H), 4.8 (d, 2H), 5.3 (1H, $C_6$—H), 5.4 (q, 2H), 6.0 (1H, $C_7$—H, 7.1 (1H, CH), 7.5, 7.8, 8.5, 9.9, 10.6 (6H, Ar—H)

IR KBr ($v_{c=0}$) 1780.1cm$^{-1}$

EXAMPLE 6

Preparation of 7-β-[(Z)-2-(2-aminothiazol-4-yl)-2-fluoromethoxyiminoacetamido]-3-(pyrrolo[1,2-a]pyrazinium-2-yl)methyl -3-cephem-4-carboxylate m.p.: 217° C.(decomposed)

NMR (DMSO-d$_6$, δ) 3.6 (q, 2H, C$_2$—H), 5.27 (d,1H), 5.3 (q, 2H, C$_3$$^1$—H), 5.7 (d, 2H), 7.15 (s, 1H), 7.4 (d, 1H) 7.75 (d, 2H), 8.4 (d, 1H), 8.8 (d, 1H) 9.6 (s, 1H),
IR KBr (ν$_{c=o}$) 1775.5cm$^{-1}$

EXAMPLE 7

Preparation of 7-β-[(Z)-2-(2-aminothiazol-4-yl)-2-hydroxyiminoacetamido]-3-(pyrrolo[1,2-a]pyrazinium-2-yl)methyl-3-cephem-4-carboxylate
m.p.: 222° C.(decomposed)
NMR(DMSO-d$_6$, δ) 3.60(q, 2H, C$_2$—H), 5.30 (d, 1H, C$_6$—H),5.30–5.50 (d- d, 2H, C$_3$$^1$—H), 6.01(d, 1H, C$_7$—H), 6.90 (s, 1H,aminothiazol-C$_5$—H), 7.44 (s, 1H),7.98 (s, 2H) 8.50 (s, 1H), 8.85 (d, 1H), 9.63(d, 1H)
IR KBr (ν$_{c=o}$) 1785.5cm$^{-1}$

EXAMPLE 8

Preparation of 7-β-[(Z)-2-(2-aminothiazol-4-yl)-2-methoxyiminoacetamido]-3-[6-(2-hydroxyethylthio)pyrrolo[1,2-a]pyrazinium-2-yl]methyl-3-cephem-4-carboxylate
m.p.: 231° C.(decomposed)
NMR(DMSO-d$_6$, δ) 3.20 (m, 2H),3.6(m, 2H & q, 2H), 4.0 (s, 3H),5.35 (q, 2H), 5.35 (1H, C$_6$—H), 6.0 (1H, C$_7$—H) 7.05 (s, 1H), 7.65, 7.9,9.6 (5H, Ar—H)
IR KBr (ν$_{c=o}$) 1760.7cm$^{-1}$

EXAMPLE 9

Preparation of 7-β-[(Z)-2-(2-aminothiazol-4-yl)-2-ethoxyiminoacetamido]-3-[6-(2-hydroxyethylthio)pyrrolo[1,2-a]pyrazinium-2-yl]methyl-3-cephem-4-carboxylate
m.p.: 210° C.(decomposed)
NMR(DMSO-d$_6$, δ) 1.35 (t, 3H), 3.20 (m, 2H), 3.6 (m, 2H & q, 2H), 4.0 (s, 3H) 5.35 (q, 2H), 5.35 (1H, C$_6$—H), 6.0 (1H, C$_7$—H) 7.05 (1H,CH), 7.65, 7.9, 9.6 8.75, 9.6 (5H, Ar—H)
IR KBr (ν$_{c=o}$) 1759.4cm$^{-1}$

EXAMPLE 10

Preparation of 7-β-[(Z)-2-(2-aminothiazol-4-yl)-2-fluoromethoxyiminoacetamido]-3-[6-(2-hydroxyethylthio)pyrrolo[1,2-a]pyrazinium-2-yl]methyl-3-cephem-4-carboxylate
m.p.: 198° C.(decomposed)
NMR(DMSO-d$_6$, δ) 3.14 (m, 2H), 3.51 (m, 4H), 5.23 (d, 1H, C$_6$, —H), 5.36 (dd, 2H, C$_3$—H), 5.78 (d, 2H, CH$_2$F) 5.90 (d, 1H, C$_7$—H), 7.15 (s, 1H), 7.51 (d, 1H),7.76 (d, 1H), 7.80 (d, 1H), 8.60 (d, 1H), 9.44 (s, 1H)
IR KBr (ν$_{c=o}$) 1772cm$^{-1}$

EXAMPLE 11

Preparation of 7-β-[(Z)-2-(2-aminothiazol-4-yl)-2-methoxyiminoacetamido]-3-(6-chloropyrrolo[1,2-a]pyrazinium-2-yl)methyl-3-cephem-4-carboxylate
m.p.: 197° C.(decomposed)
NMR(DMSO-d$_6$, δ) 3.6 (q, 2H), 4.0 (s, 3H), 5.4 (q, 2H), 5.35 (1H, C$_6$—H), 6.0 (1H, C$_7$—H) 7.05 (1H, CH), 7.6, 7.9, 8.0, 8.7, 9.65 (5H, Ar—H)
IR KBr (ν$_{c=o}$) 1760.5cm$^{-1}$

EXAMPLE 12

Preparation of 7-β-[(Z)-2-(2-aminothiazol-4-yl)-2-ethoxyiminoacetamido]-3-(6-chloropyrrolo[1,2-a]pyrazinium-2-yl)methyl-3-cephem-4-carboxylate
m.p.: 200° C.(decomposed)
NMR(DMSO-d$_6$, δ) 1.25 (t, 3H), 3.6(q, 2H), 4.25 (q, 2H), 5.4(q, 2H), 5.3 (1H, C$_6$—H), 6.0(1H, C$_7$—H), 7.0 (1H, CH), 7.6, 7.9, 8.7, 9.6 (5H, Ar—H)
IR KBr (ν$_{c=o}$) 1759.3cm$^{-1}$

EXAMPLE 13

Preparation of 7-β-[(Z)-2-(2-aminothiazol-4-yl)-2-methoxyiminoacetamido]-3-(6-cyanopyrrolo[1,2-a]pyrazinium-2-yl)methyl-3-cephem-4-carboxylate
m.p.: 212° C.(decomposed)
NMR(DMSO-d$_6$, δ) 3.6 (q, 2H), 4.0 (s, 3H), 5.5 (q, 2H), 5.35 (1H, C$_6$—H), 6.0 (1H, C$_7$—H), 7.05 (1H, CH), 7.9, 8.1, 8.2, 9.2, 10.0 (5H, Ar—H)
IR KBr (ν$_{c=o}$) 1761.4cm$^{-1}$, 2200cm$^{-1}$·(—CN)

EXAMPLE 14

Preparation of 7-β-[(Z)-2-(2-aminothiazol-4-yl)-2-methoxyiminoacetamido]-3-(6-nitropyrrolo[1,2-a]pyrazinium-2-yl)methyl-3-cephem-4-carboxylate
m.p.: 205° C.(decomposed)
NMR(DMSO-d$_6$, δ) 3.6 (q, 2H), 4.0 (s, 3H), 5.5 (q, 2H), 5.3 (1H, C$_6$—H), 6.0 (1H, C$_7$—H), 7.0 (1H, CH), 7.9, 8.2, 8.3, 9.2, 10.3 (5H, Ar—H)
IR KBr (ν$_{c=o}$) 1755cm$^{-1}$

EXAMPLE 15

Preparation of 7-β-[(Z)-2-(2-aminothiazol-4-yl)-2-methoxyiminoacetamido]-3-(6-carbamoylpyrrolo[1,2-a]pyrazinium-2-yl)methyl-3-cephem-4-carboxylate
m.p.: 199° C.(decomposed)
NMR(DMSO-d$_6$, δ) 3.65(q, 2H), 4.0 (s, 3H), 5.5 (q, 2H), 5.3 (1H, C$_6$—H), 6.0 (1H, C$_7$—H), 7.05 (1H, CH), 7.8, 8.0, 8.1, 9.8, (5H, Ar—H)
IR KBr (ν$_{c=o}$) 1780cm$^{-1}$

EXAMPLE 16

Preparation of 7-β-[(Z)-2-(2-aminothiazol-4-yl)-2-ethoxyiminoacetamido]-3-(6-carbamoylpyrrolo[1,2-a]pyrazinium-2-yl)methyl-3-cephem-4-carboxylate
m.p.: 199° C.(decomposed)
NMR(DMSO-d$_6$, δ) 1.5 (t, 3H), 3.6 (q, 2H), 4.2 (q, 2H), 5.3 (q, 2H)5.6 (1H, C$_6$—H), 6.0 (1H, C$_7$—H), 7.0 (1H, CH), 7.8, 8.0, 8.1, 9.8 (5, Ar—H)
IR KBr (ν$_{c=o}$) 1775cm$^{-1}$

EXAMPLE 17

Preparation of 7-β-[(Z)-2-(2-aminothiazol-4-yl)-2-methoxyiminoacetamido]-3-(6-carboxypyrrolo[1,2-a]pyrazinium-2-yl)methyl-3-cephem-4-carboxylate
m.p.: 189° C.(decomposed)
NMR(DMSO-d$_6$, δ) 3.65 (q, 2H), 4.0 (s, 3H), 5.5 (q, 2H) 5.35 (1H, C$_6$—H), 6.0 (1H, C$_7$—H), 7.05 (1H, CH), 7.8, 8.0, 8.10, 9.8, (5H, Ar—H)
IR KBr (ν$_{c=o}$) 1776.3cm$^{-1}$

EXAMPLE 18

Preparation of 7-β-[(Z)-2-(2-aminothiazol-4-yl)-2-methoxyiminoacetamido]-3-(6-acetylpyrrolo[1,2-a]pyrazinium-2-yl)methyl-3-cephem-4-carboxylate
m.p.: 180° C.(decomposed)
NMR(DMSO-d$_6$, δ) 2.6 (s, 3H), 3.65 (q, 2H), 3.95 (s, 3H), 5.5 (q, 2H), 5.2 (1H,2H, C$_6$—H), 5.9 (1H, C$_7$—H), 6.95 (1H, CH), 7.9, 8.0, 8.4, 9.0, 9.9 (5H, Ar—H)
IR KBr (ν$_{c=o}$)1763.5cm$^{-1}$

EXAMPLE 19

Preparation of 7-β-[(Z)-2-(2-aminothiazol-4-yl)-2-ethoxy-iminoacetamido]-3-(6-acetylpyrrolo[1,2-a]pyrazinium-2-yl)methyl-3-cephem-4-carboxylate m.p.: 182° C.(decomposed)

NMR(DMSO-$d_6$, δ) 1.2 (t, 3H), 2.6 (s, 3H), 3.6 (q, 2H), 4.2 (q, 3H), 5.2 (1H, 2H, $C_6$—H), 5.4 (q, 2H), 5.9 (1H, $C_7$—H), 6.95 (1H, CH), 8.0, 8.4, 9.0, 9.9 (5H, Ar—H)

IR KBr ($v_{c=o}$) 1760.6cm$^{-1}$

EXAMPLE 20

Preparation of 7-β-[(Z)-2-(2-aminothiazol-4-yl)-2-methoxy-iminoacetamido]-3-[6-(1-hydroxyethyl)pyrrolo[1,2-a]pyrazinium-2-yl]methyl-3-cephem-4-carboxylate m.p.: 198° C.(decomposed)

NMR(DMSO-$d_6$, δ) 1.55 (d, 3H), 3.45–3.63 (d-d, 2H, $C_2$—H), 3.95(s, 3H,OMe), 5.20–5.40 (q, 3H), 5.23 (d, 1H, $C_6$—H) 5.90 (d, 1H, $C_7$—H)6.97(s, 1H), 7.24(m, 1H), 7.63(m, 1H), 8.26(d, 1H), 8.63 (d, 1H), 9.50(s, 1H)

IR KBr ($v_{c=o}$) 1784.5cm$^{-1}$

EXAMPLE 21

Preparation of 7-β-[(Z)-2-(2-aminothiazol-4-yl)-2-methoxy-iminoacetamido]-3-(6-hydroxymethylpyrrolo[1,2-a]pyrazinium-2-yl)methyl-3-cephem-4-carboxylate m.p.: 212° C.(decomposed)

NMR(DMSO-$d_6$, δ) 3.45–3.65 (d-d, 2H, $C_2$—H), 3.95 (s, 3H, OMe), 4.90 (s, 2H, $CH_2$), 5.20–5.40 (d-d, 2H, $C_3^1$, —H), 5.2 (d, 1H,$C_6$—H)), 5.90 (d, 1H, $C_2$—H), 7.0 (s, 1H), 7.40 (d, 1H), 7.70–7.80 (m, 2H), 8.62 (d, 1H), 9.50 (s, 1H).

IR KBr ($v_{c=o}$) 1705cm$^{-1}$

EXAMPLE 22

Preparation of 7-β-[(Z)-2-(2-aminothiazol-4-yl)-2-fluoromethoxyiminoacetamido]-3-(6-hydroxymethylpyrrolo[1,2-a]pyrazinium-2-yl)methyl-3-cephem-4-carboxylate m.p.: 166° C.(decomposed)

NMR(DMSO-$d_6$, δ) 3.59 (d-d, 2H, $C_2$—H), 4.90 (s, 2H) 5.26–5.42(d-d, 2H), 5.30 (d, 1H), 5.63 (s, 1H), $CH_2$), 5.93 (s, 1H), 5.95 (d, 1H), 7.16 (s, 1H), 7.40 (d, 1H), 7.74 (m, 1H), 7.78 (m, 1H), 8.74 (d, 1H), 9.58 (s, 1H).

IR KBr ($v_{c=o}$) 1761cm$^{-1}$

EXAMPLE 23

Preparation of 7-β-[(Z)-2-(2-aminothiazol-4-yl)-2-carboxymethoxyiminoacetamido]-3-(6-hydroxymethylpyrrolo[1,2-a]pyrazinium-2-yl)methyl-3-cephem-4-carboxylate m.p.: 210° C.(decomposed)

NMR(DMSO-$d_6$, δ) 3.40–3.75 (d-d, 2H, $C_2$—H), 4.80 (s, 2H, $CH_2$CH), 5.02 (s, 2H, $CH_2Co_2$H), 5.30–5.50 (d-d, 2H, $C_3^1$, —H), 5.32 (d, 1H, $C_6$—H)), 6.00 (d, 1H, $C_7$—H), 7.10 (s, 1H), 7.46 (d, 1H), 7.77–7.84 (m, 2H), 8.72 (d, 1H), 9.59 (s, 1H).

IR KBr ($v_{c=o}$) 1774cm$^{-1}$

EXAMPLE 24

Preparation of 7-β-[(Z)-2-(2-aminothiazol-4-yl)-2-(2-carboxyprop-2-oxyimino)acetamido]-3-(6hydroxymethylpyrrolo[1,2-a]pyrazinium-2-yl)methyl-3-cephem-4-carboxylate m.p.: 209° C.(decomposed)

NMR(DMSO-$d_6$, δ) 1.50 (s, 6H), 3.40–3.70 (q, 2H, $C_2$—H), 5.25 (d, 1H), 5.20–5.40 (q, 2H), 6.02 (d, 1H), 7.05 (s, 1H), 7.90 (d, 2H), 8.34 (s, 1H), 8.74 (d, 1H), 10.0 (s, 1H).

IR KBr ($v_{c=o}$) 1778cm$^{-1}$

EXAMPLE 25

Preparation of 7-β-[(Z)-2-(2-aminothiazol-4-yl)-2-methoxy-iminoacetamido]-3-(6-formylpyrrolo[1,2-a]pyrazinium-2-yl)methyl-3-cephem-4-carboxylate m.p.: 187° C.(decomposed)

NMR(DMSO-$d_6$, δ) 3.54–3.84 (q, 2H, $C_2$—H), 4.04 (s, 3H), 5.30 (d, 1H), 5.28–5.70 (q, 2H), 6.02 (d, 1H), 6.82 (s, 1H), 7.05 (d, 1H), 7.50 (s, 1H), 7.74 (d, 1H), 7.84 (q, 1H), 8.63 (q, 1H), 9.67 (s, 1H), 10.23 (s, 1H).

IR KBr ($v_{c=o}$) 1770cm$^{-1}$

EXAMPLE 26

Preparation of 7-β-[(Z)-2-(2-aminothiazol-4-yl)2-ethoxy-iminoacetamido]-3-(6-formylpyrrolo[1,2-a]pyrazinium-2-yl)methyl-3-cephem-4-carboxylate m.p.: 179° C.(decomposed)

NMR(DMSO-$d_6$, δ) 1.35 (t, 3H), 3.58–3.82 (q, 2H, $C_2$—H), 4.35 (s, 2H), 5.30 (d, 1H), 5.30–5.60 (q, 2H), 6.02 (d, 1H), 7.02 (s, 1H), 7.53 (d, 1H), 7.74 (d, 1H), 7.86 (d, 1H), 8.68 (d, 1H), 9.65 (s, 1H), 10.24 (s, 1H).

IR KBr ($v_{c=o}$) 1773cm$^{-1}$

EXAMPLE 27

Preparation of 7-β-[(Z)-2-(2-aminothiazol-4-yl)2-methoxy-iminoacetamido]-3-[6-(2-aminoethylthio)pyrrolo[1,2-a]pyrazinium-2-yl]methyl-3-cephem-4-carboxylate m.p.: 166° C.(decomposed)

NMR(DMSO-$d_6$, δ) 3.21 (m, 2H), 3.28 (m, 2H), 3.57 (q, 2H, $C_2$—H), 3.94(s, 3H), 5.24 (d,1H), 5.33 (q, 2H), 5.90 (d,1H), 6.94 (s, 1H), 7.70 (d, 1H), 7.84 (m, 1H),7.84 (m, 1H), 7.90 (m, 1H, 8.74(d, 1H), 9.58 (s, 1H)

IR KBr ($v_{c=o}$) 1761cm$^{-1}$

EXAMPLE 28

Preparation of 7-β-[(Z)-2-(2-aminothiazol-4-yl)2-ethoxy-iminoacetamido]-3-[6-(2-aminoethylthio)pyrrolo[1,2-a]pyrazinium-2-yl]methyl-3-cephem-4-carboxylate m.p.: 175° C.(decomposed)

NMR(DMSO-$d_6$, δ) 1.20 (t, 3H), 3.17 (m, 2H), 3.26 (m, 2H), 3.58 (q, 2H, $C_2$—H), 4.18(q, 2H), 5.24 (d, 1H), 5.31 (q, 2H), 5.92 (d, 1H), 6.95 (s, 1H), 7.68 (d,1H), 7.81 (m, 1H),7.98 (m, 1H), 8.68 (m, 1H), 9.58 (s, 1H)

IR KBr ($v_{c=o}$)1761cm$^{-1}$

EXAMPLE 29

Preparation of 7-β-[(Z)-2-(2-aminothiazol-4-yl)2-fluoromethoxyiminoacetamido]-3-[6-(2-aminoethylthio)pyrrolo[1,2-a]pyrazinium-2-yl]methyl-3-cephem-4-carboxylate m.p.: 175° C.(decomposed)

NMR(DMSO-$d_6$, δ) 3.17 (m, 2H), 3.26 (m, 2H), 3.58 (q, 2H, $C_2$—H),5.2 (d, 1H), 5.34 (q, 2H), 5.64 (s,1H), 5.92 (d, 1H), 5.93 (s,1H), 7.12 (s, 1H),7.70 (s, 1H), 7.82 (m, 1H), 7.99(s, 1H), 8.71(d, 1H), 9.57 (s, 1H)

IR KBr ($v_{c=o}$) 1770cm$^{-1}$

EXAMPLE 30

Preparation of 7-β-[(Z)-2-(2-aminothiazol-4-yl)2-methoxy-iminoacetamido]-3-(8-hydroxymethylpyrrolo[1,2-a]pyrazinium-2-yl)methyl-3-cephem-4-carboxylate m.p.: 199° C.(decomposed)
NMR(DMSO-$d_6$+TFA-d δ) 3.45–3.74 (d-d, 2H, $C_2$—H), 4.01(s, 3H, OMe), 4.96 (s, 2H, CH—OH), 5.25–5.45 (d-d, 2H, $C_3'$—H), 5.30 (d, 1H, $C_6$—H), 5.93 (d, 1H, $C_7$—H) 7.0 (s, 1H), 7.40 (d, 1H)7.70–7.86 (m, 2H), 8.71 (d, 1H), 9.55 (s, 1H)
IR KBr ($v_{c=o}$) 1774cm$^{-1}$

EXAMPLE 31

Preparation of 7-β-[(Z)-2-(2-aminothiazol-4-yl)2-ethoxy-iminoacetamido]-3-(8-hydroxymethylpyrrolo[1,2-a]pyrazinium-2-yl)methyl-3-cephem-4-carboxylate
m.p.: 169° C.(decomposed)
NMR(DMSO-$d_6$+TFA-d δ) 1.24 (t, 3H, OEt), 3.51 (q,2H) 4.21 (q, 2H, OEt) 4.87 (s, 2H, $CH_2OH$), 5.25–5.45 (d-d, 2H, $C_3'$—H), 5.20 (d, 1H, $C_6$—H), 5.90 (d, 1H, $C_7$H) 6.96 (s, 1H), 7.30 (d, 1H) 7.60 (d, 2H), 7.74(d, 1H), 8.60 (s, 1H)$^-$, 9.44 (s, 1H)
IR KBr ($v_{c=o}$) 1764cm$^{-1}$

EXAMPLE 32

Preparation of 7-β-[(Z)-2-(2-aminothiazol-4-yl)2-fluoromethoxyiminoacetamido]-3-(8-hydroxymethylpyrrolo[1,2-a]pyrazinium-2-yl)methyl-3-cephem-4-carboxylate
m.p.: 178° C.(decomposed)
NMR(DMSO-$d_6$+TFA-d, δ) 3.59 (q, 2H), $C_2$—H), 5.01 (s, 2H) 5.26–5.58 (d-d, 2H), 5.30 (d, 1H), 5.63 (q, 2H), 5.84 (d-d, 2H), 5.97 (d, 1H), 7.20 (s, 1H), 7.40 (d, 1H), 7.68 (d, 1H), 7.84 (d, 1H), 8.63 (d, 1H), 9.50 (s, 1H)
IR KBr ($v_{c=o}$) 1764cm$^{-1}$

EXAMPLE 33

Preparation of 7-β-[(Z)-2-(2-aminothiazol-4-yl)2-methoxy-iminoacetamido]-3-(8-chloropyrrolo[1,2-a]pyrazinium-2-yl)methyl-3-cephem-4-carboxylate
m.p.: 191° C.(decomposed)
NMR(DMSO-$d_6$, δ) 3.6 (q, 2H), 4.0 (s, 3H), 5.4 (q, 2H), 5.3 (1H, $C_6$—H), 6.0 (1H, $C_7$—H), 7.0 (1H, CH), 7.6, 7.9, 8.5, 8.8, 9.8 (5H, Ar—H)
IR KBr ($v_{c=o}$)1760.1cm$^{-1}$

EXAMPLE 34

Preparation of 7-β-[(Z)-2-(2-aminothiazol-4-yl)2-methoxy-iminoacetamido]-3-(6-acetyl-8-chloropyrrolo[1,2-a]pyrazinium-2-yl)methyl-3-cephem-4-carboxylate
m.p.: 220° C.(decomposed)
NMR(DMSO-$d_6$, δ) 2.7 (s, 3H), 3.6 (q, 2H), 4.0(s,2H), 5.5(q, 2H), 5.3 (1H), C6—H), 5.9 (1H, $C_7$—H), 7.0(1H, CH), 8.2, 8.3, 9.0, 10.0 (4H, Ar—H)
IR KBr ($v_{c=o}$)1764.4cm$^{-1}$

EXAMPLE 35

Preparation of 7-β-[(Z)-2-(2-aminothiazol-4-yl)-2-ethoxy-iminoacetamido]-3-(6-acetyl-8-chloropyrrolo[1,2-a]pyrazinium-2-yl)methyl-3-cephem-4-carboxylate
m.p.: 220° C.(decomposed)
NMR(DMSO-$d_6$, δ) 1.2 (t, 3H), 2.6 (s, 3H), 3.6 (q, 2H), 4.2 (m, 2H), 5.5 (q, 2H), 5.3 (1H, $C_6$—H), 5.9 (1H,$C_7$—H), 6.95 (1H, CH), 7.2, 8.3, 9.0, 9.6 (4H, Ar—H)
IR KBr ($v_{c=o}$) 1760.5cm$^{-1}$

EXAMPLE 36

Preparation of 7-β-[(Z)-2-(2-aminothiazol-4-yl)-2-methoxy-iminoacetamido]-3-(6,8-diisopropyl-pyrrolo[1,2-a]pyrazinium-2-yl)methyl-3-cephem-4-carboxylate
m.p.: 194° C.(decomposed)
NMR(DMSO-$d_6$, δ) 1.10 (d, 12H), 3.45–3.55 (d-d, 2H, $C_2$—H),3.90(q, 2H), 4.05 (s, 3H, OMe), 5.20–5.40 (d-d, 2H, $C_2'$—H), 5.35 (d, 1H, $C_6$—H), 5.96 (d, 1H, $C_7$—H), 7.08 (s, 1H), 7.20 (s,1H), 7.64 (d, 1H, ), 8.50 (d, 1H), 9.60(d, 1H)
IR KBr ($v_{c=o}$) 1778cm$^{-1}$

EXAMPLE 37

Preparation of 7-β-[(Z)-2-(2-aminothiazol-4-yl)-2-methoxy-iminoacetamido]-3-(4-ethylpyrrolo[1,2-a]pyrazinium-2-yl)methyl-3-cephem-4-carboxylate
m.p.: 205° C.(decomposed)
NMR(DMSO-$d_6$, δ) 1.4 (t, 3H), 3.1 (q, 2H), 3.6 (q, 2H), 4.0 (s,3H), 5.4 (q, 2H), 5.3 (1H, $C_6$—H), 6.0 (1H,$C_7$—H), 7.05 (1H, CH), 7.2, 7.8, 8.4, 9.6 (5H, Ar—H)
IR KBr ($v_{c=o}$)1763.6cm$^{-1}$

EXAMPLE 38

Preparation of 7-β-[(Z)-2-(2-aminothiazol-4-yl)-2-ethoxy-iminoacetamido]-3-(4-ethylpyrrolo[1,2-a]pyrazinium-2-yl)methyl-3-cephem-4-carboxylate
m.p. : 210° C.(decomposed)
NMR(DMSO-$d_6$, δ) 1.3 & 1.4 (tt, 6H), 3.1 & 4.3 (qq, 4H), 3.6 (q,2H), 5.4 (q, 2H), 5.3 (1H, $C_6$—H), 6.0 (1H,$C_7$—H), 7.05 (1H, CH), 7.5, 7.8, 8.45, 9.6 (5H,Ar—H)
IR KBr ($v_{c=o}$) 1760.4cm$^{-1}$

EXAMPLE 39

Preparation of 7-β-[(Z)-2-(2-aminothiazol-4-yl)-2-methoxy-iminoacetamido]-3-(4-carboxypyrrolo[1,2-a]pyrazinium-2-yl)methyl-3-cephem-4-carboxylate
m.p.: 186° C.(decomposed)
NMR(DMSO-$d_6$, δ) 3.57 (q, 2H,$C_2$—H), 3.94 (s, 3H), 5.20 (m,3H), 5.50(d, 1H), 6.98 (s, 1H), 7.30 (d, 2H),7.64(m, 1H), 8.37(s, 1H), 8.76 (m, 1H) 9.50(s,1H),
IR KBr ($v_{c=o}$)1761cm$^{-1}$

EXAMPLE 40

Preparation of 7-β-[(Z)-2-(2-aminothiazol-4-yl)-2-methoxy-lminoacetamido]-3-(1-methylpyrrolo[1,2-a]pyrazinium-2-yl)methyl-3-cephem-4-carboxylate
m.p.: 189° C.(decomposed)
NMR(DMSO-$d_6$, δ) 3.05 (s, 3H), 3.6 (q, 2H), 4.05 (s, 3H), 5.45 (q, 2H), 5.3 (1H, $C_6$—H, 5.9(1H, $C_7$—H), 7.05 (1H, CH), 7.39, 7.7, 7.95, 8.4, 8.7(5H, Ar—H)
IR KBr ($v_{c=o}$)1765.6cm$^{-1}$

EXAMPLE 41

Preparation of 7-β-[(Z)-2-(2-aminothiazol-4-yl)-2-ethoxy-iminoacetamido]-3-(1-methylpyrrolo[1,2-a]pyrazinium-2-yl)methyl-3-cephem-4-carboxylate
m.p.: 183° C.(decomposed)
NMR(DMSO-$d_6$, δ) 1.26 (t, 3H, $CH_2CH_3$), 2.96 (s, 3H, Me), 3.57 (d, 2H, $C_2$—$CH_2$), 4.20 (q, 2H $CH_2CH_3$) 5.2 (d, 1H, $C_6$—H), 5.38 (q,2H, $C_2$—$CH_2$), 5.90 (1H, $C_7$—H), 6.98 (s, 1H), 7.30 (d, 1H,), 7.63(d, 1H), 7.88 (d, 1H), 8.30(s, 1H), 8.65(d, 1H)
IR KBr ($v_{c=o}$)1775cm$^{-1}$

EXAMPLE 42

Preparation of 7-β-[(Z)-2-(2-aminothiazol-4-yl)-2-ethoxyiminoacetamido]-3-(6-bromo-1-methylpyrrolo[1,2-a]pyrazinium-2-yl)methyl-3-cephem-4-carboxylate m.p.: 165° C.(decomposed)

NMR(DMSO-$d_6$, δ) 1.37 (t, 3H), 3.05 (q, 2H), 3.60 (q, 2H, $C_2$—H), 4.34(q, 2H), 5.36 (d-d, 2H), 5.51 (1H, $C_6$—H), 5.98(d, 1H, $C_7$—H),7.05 (s, 1H) 7.53(d, 1H), 7.90 (d, 1H), 8.02 (m, 1H), 8.60 (m, 1H),

IR KBr ($v_{c=o}$)1759cm$^{-1}$

EXAMPLE 43

Preparation of 7-β-[(Z)-2-(2-aminothiazol-4-yl)-2-methoxyiminoacetamido]-3- (1-methyl-6-cyanopyrrolo[1,2-a]pyrazinium-2-yl)methyl-3-cephem-4-carboxylate m.p.: 203° C.(decomposed)

NMR(DMSO-$d_6$, δ) 2.94 (s, 3H), 3.52 (q, 2H,$C_2$—H), 3.97 (s, 3H), 5.22(d, 1H), 5.41 (s, 2H, $C_3^1$—H), 5.91 (d, 2H),6.98(s, 1H), 7.41 (d, 1H),7.80 (d, 2H) 7.97(d, 1H), 8.45 (d, 1H),

IR KBr ($v_{c=o}$) 1763cm$^{-1}$

EXAMPLE 44

Preparation of 7-β-[(Z)-2-(2-aminothiazol-4-yl)-2-ethoxyiminoacetamido]-3-(6-carbamoyl-1-methylpyrrolo[1,2-a]pyrazinium-2-yl)methyl-3-cephem-4-carboxylate m.p.: 219° C.(decomposed)

NMR(DMSO-$d_6$, δ) 3.05 (s, 3H), 3.62 (q, 2H,$C_2$—H), 4.08 (s, 3H), 5.31(d, 1H), 5.43 (s, 2H, $C_3^1$—H), 5.98 (d, 2H), 7.08(s, 1H), 7.37 (m, 1H),7.80 (m, 1H) 8.38 (s, 1H), 8.72 (s, 1H),

IR KBr ($v_{c=o}$)1777cm$^{-1}$

EXAMPLE 45

Preparation of 7-β-[(Z)-2-(2-aminothiazol-4-yl)-2-methoxyiminoacetamido]-3-(6-chloro-1-methylpyrrolo[1,2-a]pyrazinium-2-yl)methyl-3-cephem-4-carboxylate m.p.: 201° C.(decomposed)

NMR(DMSO-$d_6$, δ) 3.0 (s, 3H), 3.6 (q, 2H), 4.0(s, 3H), 5.5(q, 2H), 5.3 (1H, C6—H), 6.0 (1H, $C_7$—H), 7.0 (1H, CH), 7.55, 7.9, 8.1, 8.9 (4H, Ar—H)

IR KBr ($v_{c=o}$)1762.0cm$^{-1}$

EXAMPLE 46

Preparation of 7-β-[(Z)-2-(2-aminothiazol-4-yl)-2-methoxyiminoacetamido]-3-(6-hydroxymethyl-1-methylpyrrolo[1,2-a]pyrazinium-2-yl)methyl-3-cephem-4-carboxylate m.p.: 233° C.(decomposed)

NMR(DMSO-$d_6$, δ) 2.98 (s, 3H), 3.52 (q, 2H, $C_2$—H), 3.97(s, 3H,OMe), 4.89 (s, 2H), 5.21 (d, 1H), 5.39 (q, 2H, $C_3$—H), 5.88(d, 1H, $C_7$—H), 6.97(s, 1H),7.28 (d,1H), 7.70 (d, 1H), 7.83 (d, 1H), 8.60 (d, 1H)

IR KBr ($v_{c=o}$)1769.9cm$^{-1}$

EXAMPLE 47

Preparation of 7-β-[(Z)-2-(2-amino-5-chlorothiazol-4-yl)-2-methoxyiminoacetamido]-3-(pyrrolo[1,2-a]pyrazinium-2-yl)methyl-3-cephem-4-carboxylate 0.5 g of 7-amino-3-(pyrrolo[1,2-a]pyrazinium-2-yl)methyl-3-cephem-4-carboxylate prepared in Preparation Example 24 was dissolved in a mixture of 3% aqueous sodium bicarbonate solution (20 ml) and acetonitrile (20 ml). To the reaction mixture was added 0.5 g of 2-(2-amino-5-chlorothiazol-4-yl)-2-(Z)-methoxyiminoacetic acid-N-hydroxybenzotriazol active compound; and the resulting mixture was stirred at 35° C. for 3 hours, cooled to room temperature and chromatographed over silica gel (eluent; acetonitrile:water=4:1). The eluates were concentrated under a reduced pressure to remove acetonitrile. The concentrated aqueous solution was lyophilized to obtain 0.1 g of title compound.

m.p.: 218° C.(decomposed)

NMR (DMSO-$d_6$+TFA-d, δ) 3.6 (q, 2H), 3.9 (s, 3H), 5.3 (q, 2H), 5.2(1H, $C_6$—H), 5.9 (1H, $C_7$—H), 7.5, 7.8, 8.5.8.8, 9.55 (6H, Ar—H)

IR KBr ($v_{c=o}$) 1761.2 cm$^{-1}$

EXAMPLE 48

Preparation of 7-β-[(Z)-2-(5-amino-1,2,4-thiadiazol-3-yl)-2-methoxyiminoacetamido]-3-(pyrrolo [1,2-a]pyrazinium-2-yl)methyl-3-cephem-4-carboxylate 0.5 g of 7-amino-3-(pyrrolo[1,2-a]pyrazinium-2-yl)methyl-3-cephem-4-carboxylate prepared in Preparation Example 24 was dissolved in a mixture of 3% aqueous sodium bicarbonate solution (20 ml) and acetonitrile (20 ml). To the reaction mixture was added 0.45 g of 2-(5-amino-1,2,4-thiadiazol-3-yl)-2-(Z)-methoxyiminoacetic acid-N-hydroxybenzotriazol active compound; and the reaction mixture was stirred at 35° C. for 8 hours, cooled to room temperature and chromatographed over silica gel(eluent; acetonitrile: water=4:1). The eluates were concentrated under a reduced pressure. The concentrated aqueous solution was lyophilized to obtain 0.1 g of title compound.

m.p.: 186° C.

NMR (DMSO-$d_6$, δ) 3.65 (s, 2H), 4.0 (s, 3H), 5.4 (q, 2H), 5.3 (1H, $C_6$—H), 6.0 (1H, $C_6$—H), 7.45, 7.8, 8.45, 8.85, 9.6 (5H, Ar—H)

IR:KBr ($v_{c=o}$) 1760 cm$^{-1}$

EXAMPLE 49

Preparation of 7-β-[(Z)-2-(2-amino-5-chlorothiazol-4-yl)-2-methoxyiminoacetamido]-3-(6-hydroxymethylpyrrolo[1,2-a]-pyrazinium-2-yl)methyl-3-cephem-4-carboxylate The same procedures as described in Example 47 were repeated using the cephem compound prepared in Preparation Example 25 to obtain title compound m.p.: 223° C.(decomposed)

NMR: (DMSO-$d_6$+TFA-d, δ) 3.60 (q, 2H, $C_2$—H), 3.86(s, 3H, OMe), 4.95 (s,2H), 5.22 (d, 1H, $C_6$—H), 5.31(q, 2H, $C_3'$—H),5.90 (d, 1H, $C_7$—H), 7.43 (d, 1H), 7.80 (m,2H), 8.70 (d, 1H), 9.50 (s, 1H)

IR:KBr ($v_{c=o}$) 1760.9 cm$^{-1}$

EXAMPLE 50

Preparation of 7-β-[(Z)-2-(5-amino-1,2,4-thiadiazol-3-yl)-2-methoxyiminoacetamido]-3-(6-hydroxymethylpyrrolo[1,2-a]-pyrazinium-2-yl)methyl-3-cephem-4-carboxylate The same procedures as described in Example 48 were repealed using cephem compound prepared in Preparation Example 25 to obtain title compound.

m.p.: 201° C.(decomposed)

NMR (DMSO-$d_6$+TFA-d, δ) 3.45–3.70 (dd, 2H, $C_2$—H), 3.98 (s, 3H, OMe), 4.95 (s, 2H), 5.25–5.50 (q, 2H, $C_3$—H), 5.25 (d, 1H, $C_6$—H), 6.01 (d, 1H, $C_7$—H), 7.40 (d, 1H), 7.74 (m, 1H), 7.85(m, 1H), 8.70 (d, 1H), 9.58 (s, 1H)

IR:KBr ($v_{c=o}$) 1757 cm$^{-1}$

EXAMPLE 51

Preparation of 7-β-[(Z)-2-(5-amino-1,2,4-thiadiazol-3-yl)-2-methoxyiminoacetamido]-3-[6-(1-hydroxyethyl)pyrrolo[1,2-a]-pyrazinium-2-yl]methyl-3cephem-4-carboxylate The same procedures as described in Example 48 were repeated using the cephem compound prepared in Preparation Example 16 to obtain title compound.

m.p.: 212° C.(decomposed)

NMR (DMSO-$d_6$+TFA-d, δ) 1.60 (d, 3H), 3.50–3.70 (dd, 2H, $C_2$—H), 3.98 (s, 3H, OMe), 5.20–5.40 (m, 3H), 5.25 (d, 1H, $C_6$—H), 5.98 (d, 1H, $C_7$—H),7.34 (s, 1H), 7.70 (m, 1H), 8.35 (s, 1H), 8.75 (m, 1H), 9.76 (s, 1H)

IR:KBr ($v_{c=o}$) 1781 cm$^{-1}$

EXAMPLE 52

Preparation of 7-β-[(Z)-2-(2-amino-5-chlorothiazol-4-yl)-2-methoxyiminoacetamido]-3-[6-(2-hydroxyethylthio)pyrrolo[1,2-a]-pyrazinium-2-yl]methyl-3-cephem-4-carboxylate The same procedures as described in Example 47 were repeated using the cephem compound prepared in Preparation Example 30 to obtain title compound.

m.p.: 178° C.(decomposed)

NMR (DMSO-$d_6$, +TFA-d, δ) 3.17 (m, 2H), 3.61 (m, 4H), 3.89 (s, 3H),5.20 (d,1H, $C_6$—H), 5.30 (q, 2H, $C_3'$—H), 5.90 (d, 1H, $C_7$—H), 7.50 (d, 1H), 7.80(m, 2H), 8.60 (d, 1H), 9.44 (s, 1H)

IR:KBr ($v_{c=o}$) 1768 cm$^{-1}$

EXAMPLE 53

Preparation of 7-β-[(Z)-2-(5-amino-1,2,4-thiadiazol-3-yl)-2-methoxyiminoacetamido]-3-[6-(2-hydroxyethylthio)pyrrolo[1,2-a]-pyrazinium-2-yl]methyl-3-cephem-4-carboxylate The same procedures as described in Example 48 were repeated using the cephem compound prepared in Preparation Example 30 to obtain title compound.

m.p.: 192° C.

NMR (DMSO-$d_6$, +TFA-d, δ) 3.20 (m, 2H), 3.6 (m, 4H), 3.93 (s, 3H),5.21 (d, 1H, $C_6$—H), 5.30 (q, 2H, $C_3'$—H), 5.90 (d, 1H, $C_7$—H), 7.60 (d, 1H), 7.80(m, 2H), 8.63 (d, 1H), 9.44 (s, 1H)

IR:KBr ($v_{c=o}$) 1757 cm$^{-1}$

EXAMPLE 54

Preparation of 7-β-[(Z)-2-(2-amino-5-chlorothiazol-4-yl)-2-methoxyiminoacetamido]-3-(8-hydroxymethylpyrrolo[1,2-a]-pyrazinium-2-yl)methyl-3-cephem-4-carboxylate The same procedures as described in Example 47 were repeated using the cephem compound prepared in Preparation Example 28 to obtain title compound.

m.p.: 208° C.

NMR (DMSO-d6, +TFA-d, δ) 3.54 (q, 2H, $C_2$—H), 3.86 (s, 3H, OMe), 4.92 (s, 2H), 5.10 (d, 1H, $C_6$—H), 5.22 (d,1H, $C_3'$—H), 5.38 (d, 1H, $C_3'$—H), 5.88 (d, 1H,$C_7$—H), 7.37 (d, 1H), 7.70 (d, 1H), 7.77 (d, 1H), 8.83 (d, 1H), 9.48 (s, 1H)

IR:KBr ($v_{c=o}$) 1777 cm$^{-1}$

EXAMPLE 55

Preparation of 7-β-[(Z)-2-(5-amino-1,2,4-thiadiazol-3-yl)-2-methoxyiminoacetamido]-3-(8-hydroxymethylpyrrolo[1,2-a]-pyrazinium-2-yl)methyl-3-cephem-4-carboxylate The same procedures as described in Example 48 were repeated using the cephem compound prepared in Preparation Example 28 to obtain title compound.

m.p.: 187° C.(decomposed)

NMR (DMSO-$_6$, +TFA-d, δ) 3.40–3.60 (dd, 2H, $C_2$—H), 3.98 (s, 3H,OMe), 4.90 (s, 2H, $CH_2OH$), 5.20 (d, 2H, $C_6$—H), 5.23–5.40 (d-d, 2H, $C_3'$—H), 5.96 (d, 1H, $C_7$—H), 7.37 (d, 1H), 7.68(d, 1H), 7.75 (d, 1H), 8.64 (d, 1H), 9.48 (s, 1H)

IR:KBr ($v_{c=o}$) 1771 cm$^{-1}$

EXAMPLE 56

Preparation of 7-β-[(Z)-2-(2-amino-5-chlorothiazol-4-yl)-2-methoxyiminoacetamido]-3-(1-methylpyrrolo[1,2-a]-pyrazinium-2-yl)methyl-3-cephem-4-carboxylate The same procedures as described in Example 47 were repeated using the cephem compound prepared in Preparation Example 29 to obtain title compound.

m.p.: 215° C.(decomposed)

NMR (DMSO-$d_6$, +TFA-d, δ) 3.90 (s, 3H), 3.60 (q, 2H, $C_2$—H), 4.02 (s,3H, OMe), 5.32 (d, 1H, $C_6$—H), 5.48 (q, 2H, $C_3'$—H), 6.01 (d, 1H, $C_7$—H), 7.39 (m,1H), 7.79 (d, 2H), 7.90 (m, 1H), 8.40 (s,1H), 8.80 (d, 1H)

IR:KBr ($v_{c=o}$) 1747.6 cm–1 EXAMPLE 57

Preparation of 7-β-[(Z)-2-(5-amino-1,2,4-thiadiazol-3-yl)-2-methoxyiminoacetamido]-3-(1-methylpyrrolo[1,2-a]-pyrazinium-2-yl)methyl-3-cephem-4-carboxylate The same procedures as described in Example 48 were repeated using the cephem compound prepared in Preparation Example 29 to obtain title compound.

m.p.: 181° C.(decomposed)

NMR (DMSO-$d_6$, +TFA-d, δ) 2.97 (s, 3H), 3.50 (q, 2H, $C_2$—H), 3.98 (s,3H, OMe), 5.20–5.50 (dd, 2H), 5.18 (d, 1H, $C_6$—H), 5.90 (d, 1H, $C_7$—H), 7.36 (m,1H), 7.66 (m, 1H), 7.90 (d, 1H), 8.34 (s, 1H), 8.70 (s, 1H)

IR:KBr ($v_{c=o}$) 1760 cm$^{-1}$

EXAMPLE 58

Preparation of 7-β-[(Z)-2-(2-amino-5-chlorothiazol-4-yl)-2-methoxyiminoacetamido]-3-(6-hydroxymethyl-1-methylpyrrolo[1,2-a]-pyrazinium-2-yl)methyl-3-cephem-4-carboxylate The same procedures as described in Example 47 were repeated using the cephem compound prepared in Preparation Example 30 to obtain title compound.

m.p.: 245° C.(decomposed)

NMR (DMSO-$d_6$, +TFA-d, δ) 3.30 (s, 3H), 3.60 (q, 2H, $C_2$—H), 3.90 (s,3H, OMe), 4.90 (s, 2H), 5.22 (d, 1H), 5.31 (q, 2H, $C_3'$—H), 5.90 (d, 1H, $C_7$—H), 7.38 (d, 1H), 7.74 (d, 1H), 7.93 (d, 1H), 8.60 (d, 1H)

IR:KBr ($v_{c=o}$) 1774 cm$^{-1}$

EXAMPLE 59

Preparation of 7-β-[(Z)-2-(5-amino-1,2,4-thiadiazol-3-yl)-2-methoxyiminoacetamido]-3-(6-bromo -1-methylpyrrolo[1,2-a]pyrazinium-2-yl)methyl-3-cephem-4-carboxylate The same procedures as described in Example 48 were repeated using the cephem compound prepared in Preparation Example 31 to obtain title compound.

m.p.: 178° C.(decomposed)

NMR (DMSO-$d_6$, +TFA-d, δ) 2.99 (s, 3H), 3.50 (q, 2H, $C_2$—H), 3.96 (s,3H, OMe), 5.30–5.50 (d-d, 2H), 5.21 (d, 1H, $C_6$—H), 5.90 (d, 1H, $C_7$—H), 6.97 (s,1H), 7.60 (d, 1H), 7.80 (d, 1H), 8.09 (d, 1H), 8.62 (d, 1H)

IR:KBr ($v_{c=o}$) 1760 cm$^{-1}$

Test Example

In order to illustrate the surprisingly superior antibacterial activity of the compounds of the present invention, the minimal inhibitory concentrations (MIC) of the compounds synthesized in the above Examples were determined and compared with Ceftazidime and Cefotaxime which were used as the control compounds.

These MIC values were determined by agar dilution method: that is, two-fold dilutions of each of the test compounds were made and dispersed in a Mueller-Hinton agar medium; standard test strain which had the 10$^6$ CFU (Colony Forming Unit) per ml was inoculated on the medium with microplanter (Toyo, Japan), and incubated at 35°–37° C. for 17±1 hours. The results of the MIC test are shown in Table 2. The structures of Ceftazidime (CAZ) and Cefotaxime (CTX) which are used as control compounds are as follows:

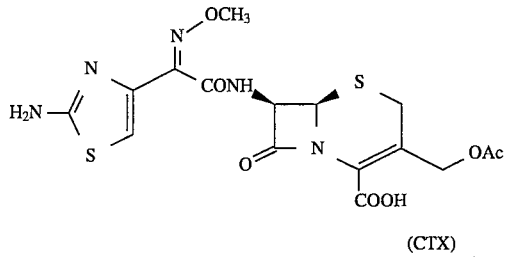

(CTX)

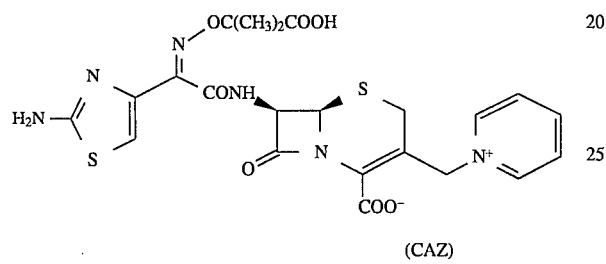

(CAZ)

TABLE 2

Minimal Inhibitory Concentration (MIC) of test compounds (μg/ml)

| Test Strain | Ex. 1-1 | Ex. 2 | Ex. 3 | Ex. 4 | Ex. 5 | Ex. 6 | Ex. 7 |
|---|---|---|---|---|---|---|---|
| 1 B. subtilis ATCC 6633 | 0.100 | 3.130 | 0.100 | 0.780 | 0.100 | 0.200 | 0.200 |
| 2 Staph. aureus ATCC 6538P | 0.100 | 3.130 | 0.100 | 0.200 | 0.200 | 0.200 | 0.100 |
| 3 Staph. aureus Smith | 0.390 | 12.500 | 0.390 | 0.390 | 0.200 | 0.390 | 0.390 |
| 4 Staph. aureus C-57 | 25.000 | 100.000 | 6.250 | 25.000 | 12.500 | 25.000 | 25.000 |
| 5 Staph. aureus C-5113 | 0.780 | 25.000 | 0.390 | 0.390 | 0.200 | 1.560 | 0.390 |
| 6 Staph. aureus C-5216 | 0.780 | 12.500 | 0.390 | 0.780 | 0.200 | 0.780 | 0.390 |
| 7 S. epidermidis ATCC 12228 | 0.025 | 1.560 | 0.025 | 0.100 | 0.025 | 0.100 | 0.025 |
| 8 Ent. aerogenes IFO 12979 | ≦0.006 | 0.025 | 0.012 | 0.012 | ≦0.006 | 0.012 | 0.100 |
| 9 Ent. cloacae IFO 13535 | 0.050 | 3.130 | 0.200 | 0.780 | 0.025 | 0.050 | 0.390 |
| 10 E. coli NIHJ JC-2 | ≦0.006 | 0.200 | 0.025 | 0.390 | 0.012 | 0.012 | 0.050 |
| 11 E. coli No. 29 | ≦0.006 | 0.100 | ≦0.006 | 0.012 | ≦0.006 | ≦0.006 | 0.050 |
| 12 E. coli DY-1 | ≦0.006 | 0.050 | ≦0.006 | ≦0.006 | ≦0.006 | ≦0.006 | 0.050 |
| 13 K. pneumoniae NCTC 9632 | ≦0.006 | 0.200 | ≦0.006 | 0.050 | ≦0.006 | 0.012 | 0.100 |
| 14 M. morganii DY-1 | ≦0.006 | 0.050 | ≦0.006 | 0.050 | ≦0.006 | ≦0.006 | 0.100 |
| 15 Ps. aeruginosa ATCC 10145 | 0.390 | 0.780 | 0.200 | 1.560 | 0.390 | 0.390 | 1.560 |
| 16 Ps. aeruginosa NCTC 10490 | 0.100 | 0.390 | 0.200 | 0.780 | 0.200 | 0.200 | 0.390 |
| 17 Ps. aeruginosa DY-2 | 1.560 | 6.250 | 0.780 | 6.250 | 1.560 | 3.130 | 25.000 |
| 18 P. vulgaris NCTC 8313 | ≦0.006 | ≦0.006 | ≦0.006 | 0.012 | ≦0.006 | ≦0.006 | 0.200 |
| 19 Prov. stuartii IFO 12930 | ≦0.006 | 0.025 | 0.012 | 0.050 | ≦0.006 | ≦0.006 | 0.012 |
| 20 Ser. marcescens IFO 12648 | ≦0.006 | 0.100 | ≦0.006 | 0.100 | ≦0.006 | 0.012 | 0.100 |

| Test strain | Ex. 8 | Ex. 9 | Ex. 10 | Ex. 11 | Ex. 12 | Ex. 13 | Ex. 14 |
|---|---|---|---|---|---|---|---|
| 1 B. subtilis ATCC 6633 | 0.100 | 0.100 | 0.100 | 0.100 | 0.100 | 0.200 | 0.390 |
| 2 Staph. aureus ATCC 6538P | 0.100 | 0.100 | 0.100 | 0.200 | 0.200 | 0.390 | 0.390 |
| 3 Staph. aureus Smith | 0.200 | 0.100 | 0.100 | 0.390 | 0.390 | 1.560 | 1.560 |
| 4 Staph. aureus C-57 | 25.000 | 12.500 | 12.500 | 12.500 | 12.500 | 25.000 | 25.000 |
| 5 Staph. aureus C-5113 | 0.390 | 0.390 | 0.390 | 0.780 | 0.780 | 0.780 | 3.130 |
| 6 Staph. aureus C-5216 | 0.780 | 0.780 | 0.780 | 0.780 | 0.780 | 0.780 | 1.560 |
| 7 S. epidermidis ATCC 12228 | 0.100 | 0.050 | 0.050 | 0.025 | 0.050 | 0.100 | 0.050 |
| 8 Ent. aerogenes IFO 12979 | 0.012 | 0.050 | 0.050 | ≦0.006 | 0.025 | 0.012 | 0.050 |
| 9 Ent. cloacae IFO 13535 | 1.560 | 0.200 | 0.200 | 0.050 | 0.390 | 0.050 | 0.780 |
| 10 E. coli NIHJ JC-2 | 0.012 | 0.025 | 0.025 | ≦0.006 | 0.050 | 0.012 | 0.100 |
| 11 E. coli No. 29 | ≦0.006 | ≦0.006 | ≦0.006 | ≦0.006 | 0.012 | 0.012 | 0.050 |
| 12 E. coli DY-1 | ≦0.006 | ≦0.006 | ≦0.006 | ≦0.006 | 0.012 | 0.012 | 0.050 |
| 13 K. pneumoniae NCTC 9632 | 0.012 | 0.025 | 0.025 | ≦0.006 | 0.025 | 0.025 | 0.050 |
| 14 M. morganii DY-1 | 0.025 | 0.012 | 0.012 | ≦0.006 | 0.025 | 0.025 | 0.050 |
| 15 Ps. aeruginosa ATCC 10145 | 0.780 | 3.130 | 0.780 | 0.780 | 1.560 | 0.780 | 6.250 |

TABLE 2-continued

| Minimal Inhibitory Concentration (MIC) of test compounds (μg/ml) | | | | | | | |
|---|---|---|---|---|---|---|---|
| 16 *Ps. aeruginosa* NCTC 10490 | 0.200 | 0.200 | 0.200 | 0.390 | 0.390 | 0.390 | 1.560 |
| 17 *Ps. aeruginosa* DY-2 | 3.130 | 3.130 | 3.130 | 3.130 | 6.250 | 3.130 | 25.000 |
| 18 *P. vulgaris* NCTC 8313 | 0.012 | ≦0.006 | 0.012 | ≦0.006 | 0.012 | ≦0.006 | 0.012 |
| 19 *Prov. stuartii* IFO 12930 | ≦0.006 | 0.025 | ≦0.006 | ≦0.006 | 0.025 | ≦0.006 | ≦0.006 |
| 20 *Ser. marcescens* IFO 12648 | 0.012 | 0.050 | 0.012 | 0.012 | 0.025 | 0.012 | 0.100 |

| Test strain | Ex. 15 | Ex. 16 | Ex. 17 | Ex. 18 | Ex. 19 | Ex. 20 | Ex. 21 |
|---|---|---|---|---|---|---|---|
| 1 *B. subtilis* ATCC 6633 | 0.050 | 0.100 | 0.100 | 0.200 | 0.100 | 0.100 | 0.100 |
| 2 *Staph. aureus* ATCC 6538P | 0.200 | 0.200 | 0.390 | 0.200 | 0.200 | 0.200 | 0.200 |
| 3 *Staph. aureus* Smith | 0.390 | 0.780 | 0.780 | 0.780 | 0.780 | 0.780 | 0.780 |
| 4 *Staph. aureus* C-57 | 12.500 | 12.500 | 25.000 | 25.000 | 50.000 | 50.000 | 50.000 |
| 5 *Staph. aureus* C-5113 | 0.780 | 1.560 | 1.560 | 0.780 | 1.560 | 1.560 | 3.130 |
| 6 *Staph. aureus* C-5216 | 0.780 | 1.560 | 1.560 | 1.560 | 1.560 | 1.560 | 0.780 |
| 7 *S. epidermidis* ATCC 12228 | 0.025 | 0.050 | 0.100 | 0.050 | 0.050 | 0.200 | 0.200 |
| 8 *Ent. aerogenes* IFO 12979 | ≦0.006 | 0.025 | 0.025 | 0.012 | 0.012 | ≦0.006 | ≦0.006 |
| 9 *Ent. cloacae* IFO 13535 | 0.100 | 0.780 | 0.390 | 0.100 | 0.200 | 0.100 | 0.100 |
| 10 *E. coli* NIHJ JC-2 | ≦0.006 | 0.100 | 0.025 | 0.012 | 0.050 | 0.025 | 0.012 |
| 11 *E. coli* No. 29 | ≦0.006 | 0.050 | 0.012 | 0.025 | 0.050 | ≦0.006 | ≦0.006 |
| 12 *E. coli* DY-1 | ≦0.006 | 0.025 | 0.025 | 0.012 | 0.025 | ≦0.006 | ≦0.006 |
| 13 *K. pneumoniae* NCTC 9632 | ≦0.006 | 0.025 | 0.025 | 0.025 | 0.050 | 0.012 | 0.012 |
| 14 *M. morganii* DY-1 | ≦0.006 | 0.025 | 0.025 | 0.025 | 0.025 | 0.012 | 0.012 |
| 15 *Ps. aeruginosa* ATCC 10145 | 0.390 | 1.560 | 1.560 | 1.560 | 3.130 | 0.780 | 0.390 |
| 16 *Ps. aeruginosa* NCTC 10490 | 0.100 | 0.390 | 0.200 | 0.200 | 0.100 | 0.200 | 0.100 |
| 17 *Ps. aeruginosa* DY-2 | 3.130 | 6.250 | 3.130 | 6.250 | 6.250 | 3.130 | 6.250 |
| 18 *P. vulgaris* NCTC 8313 | 0.012 | 0.012 | 0.012 | 0.012 | ≦0.006 | 0.012 | ≦0.006 |
| 19 *Prov. stuartii* IFO 12930 | ≦0.006 | 0.025 | ≦0.006 | 0.012 | 0.050 | ≦0.006 | ≦0.006 |
| 20 *Ser. marcescens* IFO 12648 | 0.012 | 0.100 | 0.050 | 0.012 | 0.100 | 0.025 | 0.012 |

| Test strain | Ex. 22 | Ex. 23 | Ex. 24 | Ex. 25 | Ex. 26 | Ex. 27 | Ex. 28 |
|---|---|---|---|---|---|---|---|
| 1 *B. subtilis* ATCC 6633 | 0.100 | 0.780 | 1.560 | 0.390 | 0.390 | 0.100 | 0.100 |
| 2 *Staph. aureus* ATCC 6538P | 0.200 | 1.560 | 0.390 | 0.780 | 1.560 | 0.200 | 0.200 |
| 3 *Staph. aureus* Smith | 0.780 | 6.250 | 3.130 | 3.130 | 3.130 | 0.780 | 0.780 |
| 4 *Staph. aureus* C-57 | 50.000 | 100.000 | 100.000 | 25.000 | 100.000 | 100.000 | 50.000 |
| 5 *Staph. aureus* C-5113 | 1.560 | 6.250 | 1.560 | 3.130 | 3.130 | 0.780 | 0.780 |
| 6 *Staph. aureus* C-5216 | 0.780 | 12.500 | 6.250 | 1.560 | 3.130 | 0.780 | 0.780 |
| 7 *S. epidermidis* ATCC 12228 | 0.025 | 0.390 | 0.390 | 0.100 | 0.100 | 0.050 | 0.050 |
| 8 *Ent. aerogenes* IFO 12979 | ≦0.006 | 0.012 | 0.200 | 0.025 | 0.050 | ≦0.006 | 0.012 |
| 9 *Ent. cloacae* IFO 13535 | 0.050 | 0.200 | 6.250 | 0.780 | 3.130 | 0.100 | 0.200 |
| 10 *E. coli* NIHJ JC-2 | ≦0.006 | 0.025 | 3.130 | 0.025 | 0.100 | ≦0.006 | 0.025 |
| 11 *E. coli* No. 29 | ≦0.006 | 0.025 | 1.560 | 0.050 | 0.050 | ≦0.006 | 0.012 |
| 12 *E. coli* DY-1 | ≦0.006 | 0.025 | 0.780 | 0.050 | 0.050 | ≦0.006 | 0.012 |
| 13 *K. pneumoniae* NCTC 9632 | ≦0.006 | 0.012 | 0.780 | 0.050 | 0.200 | 0.012 | 0.050 |
| 14 *M. morganii* DY-1 | ≦0.006 | 0.012 | 0.780 | 0.050 | 0.200 | 0.012 | 0.050 |
| 15 *Ps. aeruginosa* ATCC 10145 | 0.390 | 0.780 | 12.500 | 3.130 | 6.250 | 0.780 | 1.560 |
| 16 *Ps. aeruginosa* NCTC 10490 | 0.100 | 0.390 | 6.250 | 0.390 | 1.560 | 0.200 | 0.390 |
| 17 *Ps. aeruginosa* DY-2 | 1.560 | 3.130 | 25.000 | 12.500 | 12.500 | 1.560 | 3.130 |
| 18 *P. vulgaris* NCTC 8313 | ≦0.006 | ≦0.006 | 0.050 | 0.050 | 0.025 | ≦0.006 | 0.012 |
| 19 *Prov. stuartii* IFO 12930 | ≦0.006 | ≦0.006 | 0.390 | 0.012 | 0.050 | ≦0.006 | 0.012 |
| 20 *Ser. marcescens* IFO 12648 | ≦0.006 | 0.012 | 0.390 | 0.050 | 0.100 | 0.012 | 0.050 |

| Test strain | Ex. 29 | Ex. 30 | Ex. 31 | Ex. 32 | Ex. 33 | Ex. 34 | Ex. 35 |
|---|---|---|---|---|---|---|---|
| 1 *B. subtilis* ATCC 6633 | 0.050 | 0.100 | 0.100 | 0.100 | 0.200 | 0.390 | 0.390 |
| 2 *Staph. aureus* ATCC 6538P | 0.200 | 0.200 | 0.200 | 0.200 | 0.200 | 0.780 | 1.560 |
| 3 *Staph. aureus* Smith | 0.780 | 0.780 | 1.560 | 0.780 | 0.200 | 1.560 | 1.560 |
| 4 *Staph. aureus* C-57 | 25.000 | 50.000 | 25.000 | 25.000 | 25.000 | 25.000 | 25.000 |
| 5 *Staph. aureus* C-5113 | 0.780 | 3.130 | 6.250 | 3.130 | 0.780 | 0.780 | 1.560 |
| 6 *Staph. aureus* C-5216 | 0.780 | 0.780 | 3.130 | 1.560 | 0.200 | 0.780 | 1.560 |
| 7 *S. epidermidis* ATCC 12228 | 0.050 | 0.050 | 0.200 | 0.100 | 0.050 | 0.100 | 0.100 |
| 8 *Ent. aerogenes* IFO 12979 | ≦0.006 | ≦0.006 | 0.025 | 0.025 | 0.025 | 0.025 | 0.050 |
| 9 *Ent. cloacae* IFO 13535 | 0.012 | 0.050 | 0.200 | 0.100 | 0.050 | 0.100 | 0.390 |
| 10 *E. coli* NIHJ JC-2 | ≦0.006 | ≦0.006 | 0.050 | ≦0.006 | 0.012 | 0.050 | 0.100 |
| 11 *E. coli* No. 29 | ≦0.006 | ≦0.006 | 0.012 | ≦0.006 | ≦0.006 | 0.025 | 0.050 |
| 12 *E. coli* DY-1 | ≦0.006 | ≦0.006 | ≦0.006 | ≦0.006 | ≦0.006 | 0.025 | 0.025 |
| 13 *K. pneumoniae* NCTC 9632 | ≦0.006 | 0.012 | 0.050 | 0.025 | 0.012 | 0.025 | 0.100 |
| 14 *M. morganii* DY-1 | ≦0.006 | 0.012 | 0.025 | 0.025 | ≦0.006 | 0.050 | 0.200 |
| 15 *Ps. aeruginosa* ATCC 10145 | 0.780 | 0.390 | 1.560 | 0.780 | 0.780 | 6.250 | 6.250 |
| 16 *Ps. aeruginosa* NCTC 10490 | 0.200 | 0.100 | 0.780 | 0.200 | 0.200 | 3.130 | 3.130 |
| 17 *Ps. aeruginosa* DY-2 | 6.250 | 3.130 | 3.130 | 3.130 | 1.560 | 25.000 | 25.000 |
| 18 *P. vulgaris* NCTC 8313 | ≦0.006 | 0.012 | 0.012 | 0.012 | ≦0.006 | 0.012 | 0.012 |
| 19 *Prov. stuartii* IFO 12930 | ≦0.006 | ≦0.006 | 0.025 | 0.012 | ≦0.006 | 0.025 | 0.100 |
| 20 *Ser. marcescens* IFO 12648 | ≦0.006 | 0.012 | 0.050 | 0.050 | 0.012 | 0.050 | 0.200 |

| Test strain | Ex. 36 | Ex. 37 | Ex. 38 | Ex. 39 | Ex. 40 | Ex. 41 | Ex. 42 |
|---|---|---|---|---|---|---|---|

TABLE 2-continued

| Minimal Inhibitory Concentration (MIC) of test compounds (μg/ml) | | | | | | | |
|---|---|---|---|---|---|---|---|
| 1 B. subtilis ATCC 6633 | 0.200 | 0.200 | 0.200 | 0.200 | 0.100 | 0.200 | 0.390 |
| 2 Staph. aureus ATCC 6538P | 0.390 | 0.100 | 0.200 | 0.390 | 0.050 | 0.200 | 0.390 |
| 3 Staph. aureus Smith | 3.130 | 0.200 | 0.390 | 1.560 | 0.200 | 0.390 | 1.560 |
| 4 Staph. aureus C-57 | 100.000 | 25.000 | 12.500 | 50.000 | 12.500 | 12.500 | 25.000 |
| 5 Staph. aureus C-5113 | 1.560 | 1.560 | 1.560 | 1.560 | 0.780 | 0.780 | 1.560 |
| 6 Staph. aureus C-5216 | 6.250 | 0.780 | 1.560 | 1.560 | 0.780 | 1.560 | 3.130 |
| 7 S. epidermidis ATCC 12228 | 0.200 | 0.200 | 0.100 | 0.050 | 0.050 | 0.100 | 0.100 |
| 8 Ent. aerogenes IFO 12979 | 0.200 | 0.012 | 0.025 | ≦0.006 | 0.012 | 0.025 | 0.050 |
| 9 Ent. cloacae IFO 13535 | 3.130 | 0.200 | 0.200 | 0.012 | 0.025 | 0.200 | 0.780 |
| 10 E. coli NIHJ JC-2 | 0.780 | 0.012 | 0.050 | ≦0.006 | 0.012 | 0.025 | 0.200 |
| 11 E. coli No. 29 | 0.200 | ≦0.006 | ≦0.006 | ≦0.006 | ≦0.006 | 0.012 | 0.050 |
| 12 E. coli DY-1 | 0.100 | ≦0.006 | ≦0.006 | ≦0.006 | ≦0.006 | 0.012 | 0.025 |
| 13 K. pneumoniae NCTC 9632 | 0.780 | 0.012 | 0.050 | ≦0.006 | 0.012 | 0.025 | 0.200 |
| 14 M. morganii DY-1 | 1.560 | 0.025 | 0.050 | ≦0.006 | 0.012 | 0.025 | 0.200 |
| 15 Ps. aeruginosa ATCC 10145 | 50.000 | 3.130 | 3.130 | 0.780 | 0.780 | 1.560 | 6.250 |
| 16 Ps. aeruginosa NCTC 10490 | 25.000 | 0.780 | 0.780 | 0.200 | 0.390 | 0.390 | 3.130 |
| 17 Ps. aeruginosa DY-2 | 100.000 | 6.250 | 3.130 | 6.250 | 3.130 | 3.130 | 25.000 |
| 18 P. vulgaris NCTC 8313 | 0.050 | 0.012 | 0.012 | ≦0.006 | 0.012 | ≦0.006 | 0.025 |
| 19 Prov. stuartii IFO 12930 | 0.200 | 0.012 | 0.050 | ≦0.006 | ≦0.006 | 0.012 | 0.050 |
| 20 Ser. marcescens IFO 12648 | 0.780 | 0.012 | 0.050 | ≦0.006 | 0.012 | 0.050 | 0.200 |

| Test strain | Ex. 43 | Ex. 44 | Ex. 45 | Ex. 46 | Ex. 47 | Ex. 48 | Ex. 49 |
|---|---|---|---|---|---|---|---|
| 1 B. subtilis ATCC 6633 | 0.200 | 0.390 | 0.100 | 0.390 | 0.025 | 0.200 | 0.100 |
| 2 Staph. aureus ATCC 6538P | 0.100 | 0.200 | 0.100 | 0.200 | 0.050 | 0.390 | 0.200 |
| 3 Staph. aureus Smith | 0.780 | 0.780 | 0.390 | 0.780 | 0.200 | 0.780 | 0.390 |
| 4 Staph. aureus C-57 | 12.500 | 100.000 | 6.250 | 50.000 | 1.560 | 6.250 | 1.560 |
| 5 Staph. aureus C-5113 | 1.560 | 1.560 | 0.390 | 1.560 | 0.200 | 0.780 | 0.390 |
| 6 Staph. aureus C-5216 | 0.780 | 1.560 | 0.780 | 1.560 | 0.200 | 0.780 | 0.780 |
| 7 S. epidermidis ATCC 12228 | 0.012 | 0.100 | 0.012 | 0.100 | 0.025 | 0.100 | 0.012 |
| 8 Ent. aerogenes IFO 12979 | 0.012 | 0.050 | 0.025 | 0.050 | 0.012 | 0.012 | 0.050 |
| 9 Ent. cloacae IFO 13535 | 0.200 | 0.100 | 0.050 | 0.100 | 0.390 | 0.025 | 0.390 |
| 10 E. coli NIHJ JC-2 | 0.025 | 0.050 | 0.025 | 0.050 | 0.100 | 0.012 | 0.100 |
| 11 E. coli No. 29 | 0.050 | 0.025 | 0.012 | 0.025 | 0.050 | 0.012 | 0.025 |
| 12 E. coli DY-1 | 0.012 | 0.025 | 0.012 | 0.025 | 0.012 | 0.025 | ≦0.006 |
| 13 K. pneumoniae NCTC 9632 | 0.100 | 0.050 | 0.012 | 0.050 | 0.050 | 0.025 | 0.100 |
| 14 M. morganii DY-1 | 0.050 | 0.100 | 0.012 | 0.100 | 0.050 | 0.050 | 0.100 |
| 15 Ps. aeruginosa ATCC 10145 | 0.780 | 3.130 | 3.130 | 3.130 | 0.780 | 0.390 | 1.560 |
| 16 Ps. aeruginosa NCTC 10490 | 0.780 | 0.780 | 0.390 | 0.780 | 0.050 | 0.100 | 0.200 |
| 17 Ps. aeruginosa DY-2 | 12.500 | 6.250 | 6.250 | 0.250 | 3.130 | 0.780 | 3.130 |
| 18 P. vulgaris NCTC 8313 | ≦0.006 | 0.050 | ≦0.006 | 0.050 | ≦0.006 | 0.012 | 0.025 |
| 19 Prov. stuartii IFO 12930 | 0.012 | 0.012 | ≦0.006 | 0.012 | 0.025 | ≦0.006 | ≦0.006 |
| 20 Ser. marcescens IFO 12648 | 0.050 | 0.050 | 0.025 | 0.050 | 0.100 | 0.025 | 0.100 |

| Test strain | Ex. 50 | Ex. 51 | Ex. 52 | Ex. 53 | Ex. 54 | Ex. 55 | Ex. 56 |
|---|---|---|---|---|---|---|---|
| 31 B. subtilis ATCC 6633 | 0.100 | 0.200 | 0.100 | 0.200 | 0.200 | 0.100 | 0.200 |
| 2 Staph. aureus ATCC 6538P | 0.390 | 0.780 | 0.200 | 0.780 | 0.390 | 0.780 | 0.050 |
| 3 Staph. aureus Smith | 0.780 | 1.560 | 1.560 | 3.130 | 0.780 | 1.560 | 0.390 |
| 4 Staph. aureus C-57 | 12.500 | 50.000 | 6.250 | 25.000 | 6.250 | 25.000 | 3.130 |
| 5 Staph. aureus C-5113 | 1.560 | 1.560 | 1.560 | 3.130 | 0.780 | 6.250 | 0.780 |
| 6 Staph. aureus C-5216 | 0.780 | 1.560 | 0.780 | 3.130 | 1.560 | 3.130 | 0.780 |
| 7 S. epidermidis ATCC 12228 | 0.050 | 0.100 | 0.100 | 3.390 | 0.050 | 0.200 | 0.100 |
| 8 Ent. aerogenes IFO 12979 | ≦0.006 | 0.025 | 0.100 | 0.025 | 0.100 | 0.025 | 0.100 |
| 9 Ent. cloacae IFO 13535 | 0.050 | 0.100 | 0.780 | 0.100 | 0.780 | 0.100 | 0.780 |
| 10 E. coli NIHJ JC-2 | ≦0.006 | 0.025 | 0.200 | 0.025 | 0.390 | 0.012 | 0.200 |
| 11 E. coli No. 29 | ≦0.006 | 0.025 | 0.100 | 0.050 | 0.050 | ≦0.006 | 0.050 |
| 12 E. coli DY-1 | ≦0.006 | 0.025 | 0.025 | 0.025 | 0.025 | 0.012 | 0.050 |
| 13 K. pneumoniae NCTC 9632 | 0.012 | 0.050 | 0.100 | 0.025 | 0.780 | 0.025 | 0.100 |
| 14 M. morganii DY-1 | 0.012 | 0.100 | 0.200 | 0.050 | 0.100 | 0.025 | 0.390 |
| 15 Ps. aeruginosa ATCC 10145 | 0.780 | 1.560 | 1.560 | 0.780 | 3.130 | 0.780 | 1.560 |
| 16 Ps. aeruginosa NCTC 10490 | 0.100 | 0.200 | 1.560 | 0.780 | 0.780 | 0.100 | 0.780 |
| 17 Ps. aeruginosa DY-2 | 1.560 | 3.130 | 12.500 | 6.250 | 12.500 | 1.560 | 3.130 |
| 18 P. vulgaris NCTC 8313 | 0.012 | 0.050 | 0.012 | 0.100 | 0.050 | 0.050 | 0.012 |
| 19 Prov. stuartii IFO 12930 | ≦0.006 | 0.012 | 0.025 | 0.025 | 0.025 | ≦0.006 | 0.012 |
| 20 Ser. marcescens IFO 12648 | 0.012 | 0.050 | 0.200 | 0.050 | 0.390 | 0.025 | 0.200 |

| Test strain | Ex. 57 | Ex. 58 | Ex. 59 | CTX | CAZ |
|---|---|---|---|---|---|
| 1 B. subtilis ATCC 6633 | 0.200 | 0.200 | 0.100 | 0.100 | 1.560 |
| 2 Staph. aureus ATCC 6538P | 0.100 | 0.050 | 0.100 | 0.780 | 1.560 |
| 3 Staph. aureus Smith | 0.780 | 0.390 | 0.390 | 1.560 | 6.250 |
| 4 Staph. aureus C-57 | 1.560 | 3.130 | 6.250 | 100.000 | 100.000 |
| 5 Staph. aureus C-5113 | 0.200 | 0.780 | 0.780 | 3.130 | 25.000 |
| 6 Staph. aureus C-5216 | 0.390 | 0.780 | 0.780 | 1.560 | 25.000 |
| 7 S. epidermidis ATCC 12228 | 0.050 | 0.100 | 0.050 | 0.100 | 0.780 |
| 8 Ent. aerogenes IFO 12979 | 0.025 | 0.100 | ≦0.006 | 0.025 | 0.050 |

TABLE 2-continued

| | Minimal Inhibitory Concentration (MIC) of test compounds (µg/ml) | | | | |
|---|---|---|---|---|---|
| 9 *Ent. cloacae* IFO 13535 | 0.100 | 0.780 | 0.200 | 0.780 | 1.560 |
| 10 *E. coli* NIHJ JC-2 | 0.012 | 0.200 | 0.025 | 0.050 | 0.200 |
| 11 *E. coli* No. 29 | 0.025 | 0.050 | 0.012 | ≦0.006 | 0.100 |
| 12 *E. coli* DY-1 | 0.025 | 0.050 | ≦0.006 | ≦0.006 | 0.050 |
| 13 *K. pneumoniae* NCTC 9632 | 0.012 | 0.100 | 0.025 | 0.025 | 0.050 |
| 14 *M. morganii* DY-1 | 0.050 | 0.390 | 0.025 | 0.025 | 0.100 |
| 15 *Ps. aeruginosa* ATCC 10145 | 0.780 | 1.560 | 1.560 | 6.250 | 0.780 |
| 16 *Ps. aeruginosa* NCTC 10490 | 0.200 | 0.780 | 1.560 | 0.780 | 0.100 |
| 17 *Ps. aeruginosa* DY-2 | 1.560 | 3.130 | 12.500 | 12.500 | 1.560 |
| 18 *P. vulgaris* NCTC 8313 | 0.050 | 0.012 | 0.012 | ≦0.006 | 0.025 |
| 19 *Prov. stuartii* IFO 12930 | 0.012 | 0.012 | ≦0.006 | ≦0.006 | 0.025 |
| 20 *Ser. marcescens* IFO 12648 | 0.025 | 0.200 | 0.025 | 0.050 | 0.025 |

As can be seen from Table 2, the cephalosporin compounds of the present invention possess potent and broad antibacterial activities as compared with the known broad-spectrum cephalosporin antibiotics, Ceftazidime and Cefotaxime. More specifically, the cephalosporin compounds of the present invention exhibits 2 to 10 times antibacterial activities against Gram-positive bacteria, and 2 to 4 times antibacterial activities against Gram-negative bacteria compared with those of the control compounds.

In addition, they also exhibit potent antibacterial activities over Ceftazidime against *Pseudomonas aeruginosa* which causes serious problems in human beings.

While the present invention has been shown and described with reference to the particular embodiment, it will be apparent to those skilled in the art that many changes and modifications may be made without departing from the spirit and scope of the invention as defined in the appended claims.

What is claimed is:

1. A cephalosporin compound of formula(I) or a pharmaceutically acceptable non-toxic salt thereof:

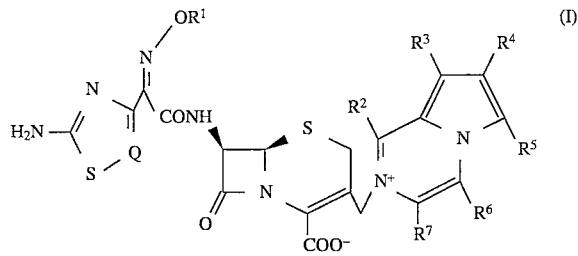

wherein:

$R^1$ is a hydrogen or an optionally halogen-substituted $C_{1-3}$ alkyl group, a propargyl group or —$C(R^a)(R^b)COOH$, wherein $R^a$ and $R^b$ are independently a hydrogen or a $C_{1-3}$ alkyl group;

$R^2$, $R^3$, $R^4$, $R^5$, $R^6$ and $R^7$ are independently a hydrogen or halogen or a $C_{1-3}$ alkyl, amino or hydroxy $C_{1-3}$ alkylthio, cyano, carbamoyl, carboxyl, hydroxy $C_{1-3}$ alkyl, nitro, acetyl or formyl group; and Q is CH, N or CCl.

2. The cephalosporin compound of formula(I) or the pharmaceutically acceptable salt thereof recited in claim 1, wherein $R^1$ is a hydrogen or a methyl, ethyl, carboxymethyl, carboxypropyl, fluoromethyl, 2-fluoroethyl or propargyl group; $R^2$ is a hydrogen or a methyl group; $R^3$ is a hydrogen or chlorine or a isopropyl or hydroxymethyl group; $R^4$ and $R^7$ are hydrogen; $R^5$ is a hydrogen, chlorine or bromine or a isopropyl, hydroxymethyl, hydroxyethyl, hydroxyethylthio, aminoethylthio, cyano, nitro, carbamoyl, carboxyl, acetyl or formyl group; $R^6$ is a hydrogen, or an ethyl or carboxyl group; and Q is CH, N or CCl.

3. The cephalosporin compound of claim 1 selected from the group consisting of:

7-β-[(Z)-2-(2-aminothiazol-4-yl)-2-methoxyiminoacetamido]3-(pyrrolo[1,2-a]pyrazinium-2-yl)methyl-3-cephem-4-carboxylate, 7-β-[(Z)-2-(2-aminothiazol-4-yl)-2-(2-carboxyprop-2-oxyimino)acetamido]-3-(pyrrolo[1,2-a]pyrazinium-2-yl)methyl-3-cephem-4-carboxylate, 7-β-[(Z)-2-(2-aminothiazol-4-yl)-2-ethoxyiminoacetamido]-3-(pyrrolo[1,2-a]pyrazinium-2-yl)methyl-3-cephem-4-carboxylate, 7-β-[(Z)-2-(2-aminothiazol-4-yl)-2-(propyn-1-oxyimino)acetamido]-3-(pyrrolo[1,2-a]pyrazinium-2-yl)methyl-3-cephem-4-carboxylate, 7-β-[(Z)-2-(2-aminothiazol-4-yl)-2-(2-fluoroethoxyimino)acetamido]-3-(pyrrolo[1,2-a]pyrazinium-2-yl)methyl-3-cephem-4-carboxylate, 7-β-[(Z)-2-(2-aminothiazol-4-yl)-2-fluoromethoxyiminoacetamido]-3-(pyrrolo[1,2-a]pyrazinium-2-yl)methyl-3-cephem-4-carboxylate, 7-β-[(Z)-2-(2-aminothiazol-4-yl)-2-hydroxyiminoacetamido]-3-(pyrrolo[1,2-a]pyrazinium-2-yl)methyl-3-cephem-4-carboxylate, 7-β-[(Z)-2-(2-aminothiazol-4-yl)-2-methoxyiminoacetamido]-3-[6-(2-hydroxyethylthio)pyrrolo[1,2-a]pyrazinium-2-yl]methyl-3-cephem-4-carboxylate, 7-β-[(Z)-2-(2-aminothiazol-4-yl)-2-ethoxyiminoacetamido]-3-6-(2-hydroxyethylthio)pyrrolo[1,2-a]pyrazinium-2-yl]methyl-3-cephem-4-carboxylate, 7-β-[(Z)-2-(2-aminothiazol-4-yl)-2-fluoromethoxyiminoacetamido]-3-[6-(2-hydroxyethylthio)pyrrolo[1,2-a]pyrazinium-2-yl]methyl-3-cephem-4-carboxylate, 7-β-[(Z)-2-(2-aminothiazol-4-yl)-2-methoxyiminoacetamido]-3-(6-chloropyrrolo[1,2-a]pyrazinium-2-yl)methyl-3-cephem-4-carboxylate, 7-62-[(Z)-2-(2-aminothiazol-4-yl)-2-ethoxyiminoacetamido]-3-(6-chloropyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-cyanopyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-nitropyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-carbamoylpyrrolo[1,2-a]pyrazinium-2-yl)methyl-3-cephem-4-carboxylate, 7-β-[(Z)-2-(2-aminothiazol-4-yl)-2-ethoxyiminoacetamido]-3-(6-carbamoylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-carboxypyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-acetylpyrrolo[1,2-a]pyrazinium-2-yl)methyl-3-cephem-4-carboxylate, 7-β-[(Z)-2-(2-aminothiazol-4-yl)-2-ethoxyiminoacetamido]-3-(6-acetylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-[6-(1-hydroxyethyl)pyrrolo[1,2-a]pyrazinium-2-yl]methyl-3-cephem-4-carboxylate, 7-β-[(Z)-2-(2-aminothiazol-4-yl)-2-methoxyiminoacetamido]-3-(6-hydroxymethylpyrrolo[1,2-a]pyrazinium-2-yl)methyl-3-cephem-4-carboxylate, 7-β-[(Z)-2-(2-aminothiazol-4-yl)-2-fluoromethoxyiminoacetamido]-3-(6-hydroxymethylpyrrolo[1,2-a]pyrazinium-2-yl)methyl-3-cephem-4-carboxylate, 7-β-[(Z)-2-(2-aminothiazol-4-yl)-2-carboxymethoxyiminoacetamido]-3-(6-hydroxymethylpyrrolo[1,2-a]pyrazinium-2-yl)methyl-3-cephem-4-carboxylate, 7-β-[(Z)-2-(2-aminothiazol-4-yl)-2-(2-carboxyprop-2-oxyimino)acetamido]-3-(6-hydroxymethylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-formylpyrrolo[1,2-a]pyrazinium-2-yl)methyl-3-cephem-4-carboxylate, 7-β-[(Z)-2-(2-aminothiazol-4-yl)-2-ethoxyiminoacetamido]-3-(6-formylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-[6-(2-aminoethylthio)pyrrolo[1,2-a]pyrazinium-2-yl]methyl-3-cephem-4-carboxylate, 7-β-[(Z)-2-(2-aminothiazol-4-yl)-2-ethoxyiminoacetamido]-3-[6-(2-aminoethylthio)pyrrolo[1,2-a]pyrazinium-2-yl]methyl-3-cephem-4-carboxylate, 7-β-[(Z)-2-(2-aminothiazol-4-yl)-2-fluoromethoxyiminoacetamido]-3-[6-(2-aminoethylthio)pyrrolo[1,2-a]pyrazinium-2-yl]methyl-3-cephem-4-carboxylate, 7-β-[(Z)-2-(2-aminothiazol-4-yl)-2-methoxylminoacetamido]-3-(8-hydroxymethylpyrrolo[1,2-a]pyrazinium-2-yl)methyl-3-cephem-4-carboxylate, 7-β-[(Z)-2-(2-aminothiazol-4-yl)-2-ethoxyiminoacetamido]-3-(8-hydroxymethylpyrrolo[1,2-a]pyrazinium-2-yl)methyl-3-cephem-4-carboxylate, 7-β-[(Z)-2-(2-aminothiazol-4-yl)-2-fluoromethoxyiminoacetamido]-3-(8-hydroxymethylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-(8-chloropyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-acetyl-8-chloropyrrolo[1,2-a]pyrazinium-2-yl)methyl-3-cephem-4-carboxylate, 7-β-[(Z)-2-(2-aminothiazol-4-yl)-2-ethoxyiminoacetamido]-3-(6-acetyl-8-chloropyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6,8-diisopropylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-(4-ethylpyrrolo[1,2-a]pyrazinium-2-yl)methyl-3-cephem-4-carboxylate, 7-β-[(Z)-2-(2-aminothiazol-4-yl)-2-ethoxyiminoacetamido]-3-(4-ethylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-(4-carboxypyrrolo[1,2-a]pyrazinium-2-yl)methyl-3-cephem-4-carboxylate, 7-β-[(Z)-2-(2-aminothiazol-4-yl)-2-methoxyiminoacetamido]-3-(1-methylpyrrolo[1,2-a]pyrazinium-2-yl)methyl-3-cephem-4-carboxylate, 7-β-[(Z)-2-(2-aminothiazol-4-yl)-2-ethoxyiminoacetamido]-3-(1-methylpyrrolo[1,2-a]pyrazinium-2-yl)methyl-3-cephem-4-carboxylate, 7-β-[(Z)-2-(2-aminothiazol-4-yl)-2-ethoxyiminoacetamido]-3-(6-bromo-1-methylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-cyano-1-methylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-carbamoyl-1-methylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-chloro-1-methylpyrrolo[1,2-a]pyrazinium-2-yl)methyl-3-cephem-4-carboxylate, 7-β-[(Z)-2-(2-aminothiazol-4-yl)-2-methoxyiminoacetamido]-3-(6-hydroxymethyl-1-methylpyrrolo[1,2-a]pyrazinium-2-yl)methyl-3-cephem-4-carboxylate, 7-β-[(Z)-2-(2-amino-5-chlorothiazol-4-yl)-2-methoxyiminoacetamido]-3-(pyrrolo[1,2-a]pyrazinium-2-yl)methyl-3-cephem-4-carboxylate, 7-β-[(Z)-2-(5-amino-1,2,4-thiadiazol-3-yl)-2-methoxyiminoacetamido]-3-(pyrrolo[1,2-a]pyrazinium-2-yl)methyl-3-cephem-4-carboxylate, 7-β-[(Z)-2-(2-amino-5-chlorothiazol-4-yl)-2-methoxyiminoacetamido]-3-(6-hydroxymethylpyrrolo[1,2-a]pyrazinium-2-yl)methyl-3-cephem-4-carboxylate, 7-β-[(Z)-2-(5-amino-1,2,4-thiadiazol-3-yl)-2-methoxyiminoacetamido]-3-(6-hydroxymethylpyrrolo[1,2-a]pyrazinium-2-yl)methyl-3-cephem-4-carboxylate, 7-β-[(Z)-2-(5-amino-1,2,4-thiadiazol-3-yl)-2-methoxyiminoacetamido]-3-[6-(1-hydroxyethyl)pyrrolo[1,2-a]pyrazinium-2-yl]methyl-3-cephem-4-carboxylate, 7-β-[(Z)-2-(2-amino-5-chlorothiazol-4-yl)-2-methoxyiminoacetamido]-3-[6-(2-hydroxyethylthio)pyrrolo[1,2-a]pyrazinium-2-yl]methyl-3-cephem-4-carboxylate, 7-β-[(Z)-2-(5-amino-1,2,4-thiadiazol-3-yl)-2-methoxyiminoacetamido]-3-[6-(2-hydroxyethylthiopyrrolo[1,2-a]pyrazinium-2-yl]methyl-3-cephem-4-carboxylate, 7-β-[(Z)-2-(2-amino-5-chlorothiazol-4-yl)-2-methoxyiminoacetamido]-3-(8-hydroxymethylpyrrolo[1,2-a]pyrazinium-2-yl)methyl-3-cephem-4-carboxylate, 7-β-[(Z)-2-(5-amino-1,2,4-thiadiazol-3-yl)-2-methoxyiminoacetamido]-3-(8-hydroxymethylpyrrolo[1,2-a]pyrazinium-2-yl)methyl-3-cephem-4-carboxylate, 7-β-[(Z)-2-(2-amino-5-chlorothiazol-4-yl)-2-methoxyiminoacetamido]-3-(1-methylpyrrolo[1,2-a]pyrazinium-2-yl)methyl-3-cephem-4-carboxylate, 7-β-[(Z)-2-(5-amino-1,2,4-thiadiazol-3-yl)-2-methoxyiminoacetamido]-3-(1-methylpyrrolo[1,2-a]pyrazinium-2-yl)methyl-3-cephem-4-carboxylate, 7-β-[(Z)-2-(2-amino-5-chlorothiazol-4-yl)-2-methoxyiminoacetamido]-3-(6-hydroxymethyl-1-methylpyrrolo[1,2-a]pyrazinium-2-yl)methyl-3-cephem-4-carboxylate, and 7-β-[(Z)-2-(5-amino-1,2,4-thiadiazol-3-yl)-2-methoxyiminoacetamido]-3-(6-bromo-1-methylpyrrolo[1,2-a]pyrazinium-2-yl)methyl-3-cephem-4-carboxylate;

or the pharmaceutically acceptable salts thereof.

4. A pharmaceutical composition comprising a therapeutically effective amount of the cephalosporin compound or the pharmaceutically acceptable salt thereof recited in claim 1 and a pharmacologically acceptable carrier.

* * * * *